United States Patent
Loffler et al.

(10) Patent No.: US 6,595,908 B2
(45) Date of Patent: Jul. 22, 2003

(54) METHOD FOR ANALYZING AMOUNT OF ACTIVITY

(75) Inventors: Edgar German Loffler, Uberlingen-Bonndorf (DE); Johann Kindlein, Oberhausen (DE); Arie Luite Visscher, Driebergen (NL); Jan D. Breemer, Kestern (NL)

(73) Assignee: Nucletron B.V., Veenendaal (NL)

( * ) Notice: Subject to any disclaimer, the term of this patent is extended or adjusted under 35 U.S.C. 154(b) by 0 days.

(21) Appl. No.: 09/788,226

(22) Filed: Feb. 16, 2001

(65) Prior Publication Data

US 2001/0053870 A1 Dec. 20, 2001

Related U.S. Application Data

(63) Continuation-in-part of application No. 09/377,382, filed on Aug. 19, 1999, now Pat. No. 6,454,696.

(30) Foreign Application Priority Data

Jul. 23, 1999 (NL) .............................. 1012697
Jan. 19, 2001 (NL) .............................. 1017149

(51) Int. Cl.[7] .......................... A61M 36/00; A61N 5/00
(52) U.S. Cl. ......................................................... 600/7
(58) Field of Search ................................. 600/1–8, 427, 600/425, 426, 428, 429, 462, 463, 464, 465, 466, 439; 606/108, 130

(56) References Cited

U.S. PATENT DOCUMENTS

| | | | |
|---|---|---|---|
| 2,269,963 A | 1/1942 | Wappler | |
| 4,086,914 A | 5/1978 | Moore | |
| 4,223,674 A | 9/1980 | Fluent | |
| 4,700,692 A | 10/1987 | Baumgartner | |
| 5,810,769 A | 9/1998 | Schlegel | |
| 5,860,909 A | 1/1999 | Mick | |
| 6,129,670 A | * 10/2000 | Burdette et al. | 600/427 |
| 6,200,255 B1 | * 3/2001 | Yu | 600/1 |
| 6,327,490 B1 | * 12/2001 | Spetz | 600/427 |
| 6,387,034 B1 | * 5/2002 | Lee | 600/1 |

FOREIGN PATENT DOCUMENTS

WO  WO 97/22379  6/1997

OTHER PUBLICATIONS

JJ Battermann, "Iodine–125 Seed Implantation for Localized Prostate Cancer," Journal of Brachytherapy International 1998, 14:21–27 (Jan. 1998).
Interplant Brochure, Burdette Medical Systems (updated).

* cited by examiner

Primary Examiner—Max F. Hindenburg
Assistant Examiner—Brian Szmal
(74) Attorney, Agent, or Firm—Birch, Stewart, Kolasch & Birch, LLP

(57) ABSTRACT

A modular device for implanting radioactive seeds in an animal body through needles implanted in the body. Trains of radioactive seeds and non-radioactive spacers are assembled in an assembly unit. The assembly unit comprises a device for determining activity of the seeds with an accuracy that allows distinguishing between different activities within tolerance ranges of specified nominal activities for the seeds. After implantation of the seeds in the body a pre-plan may be recalculated taking into consideration actual activities of seeds implanted. Not correctly composed trains may be disposed of. A post-plan may be determined based upon actually measured activities of implanted seeds.

27 Claims, 23 Drawing Sheets

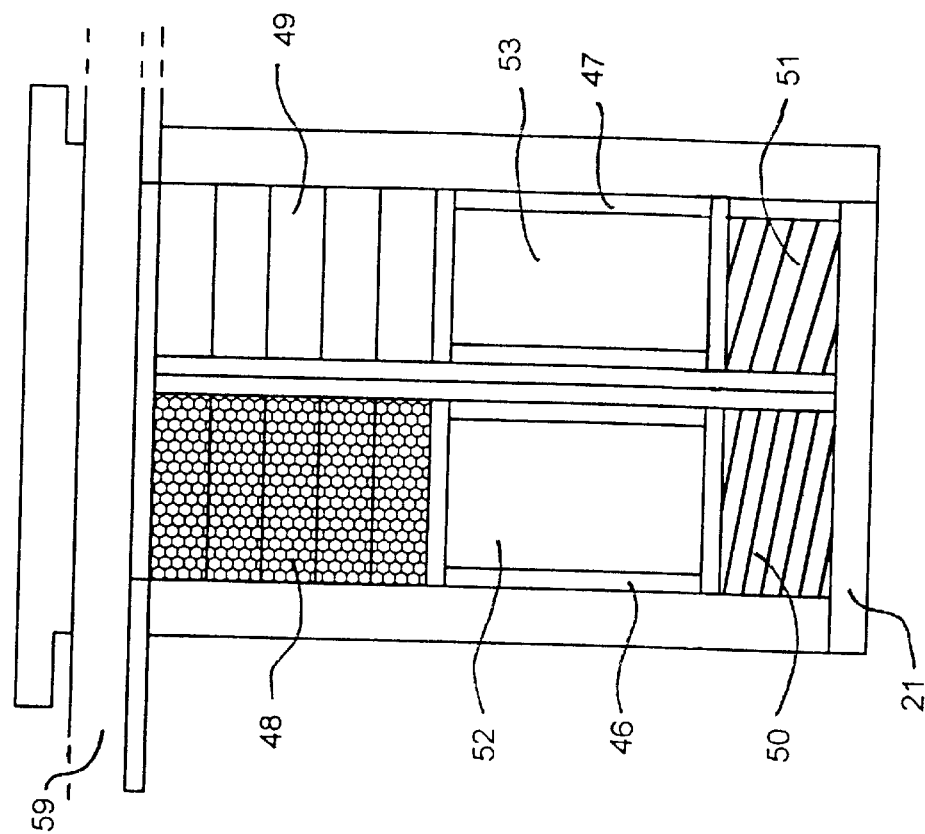
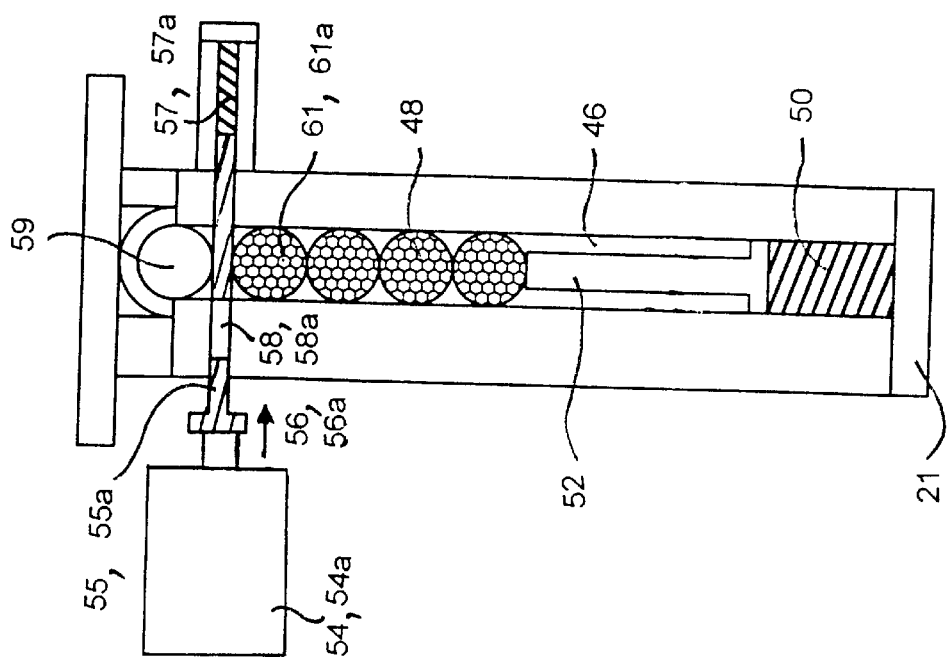
FIG. 3B
FIG. 3A

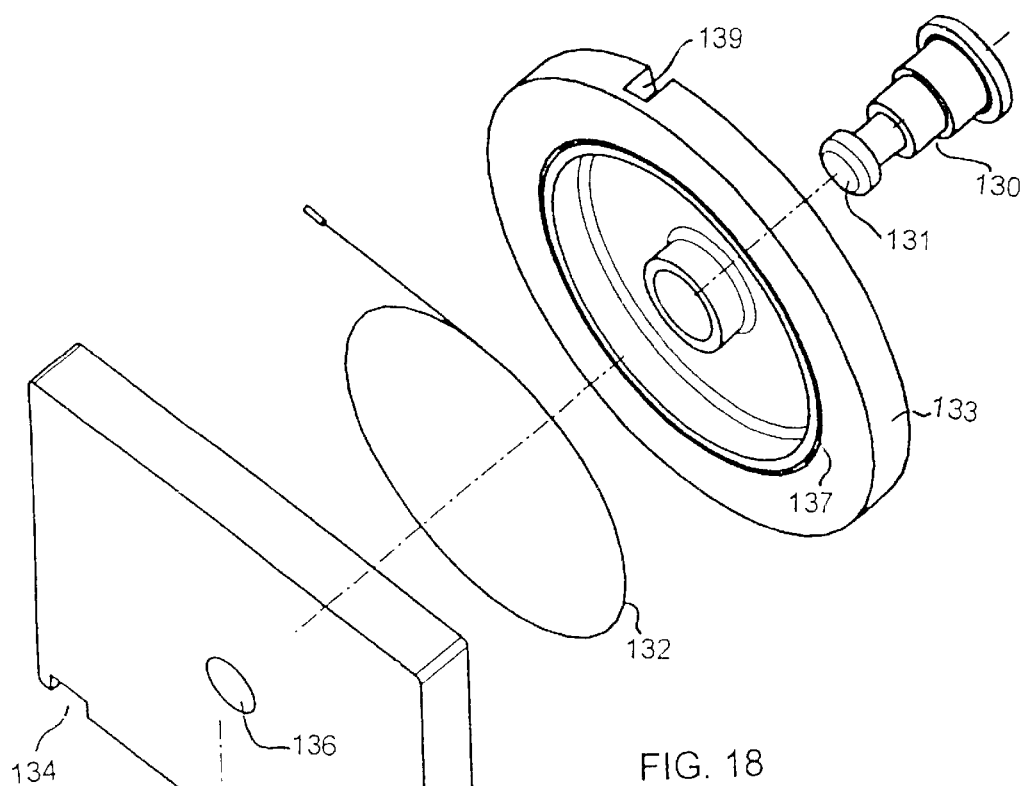
FIG. 18
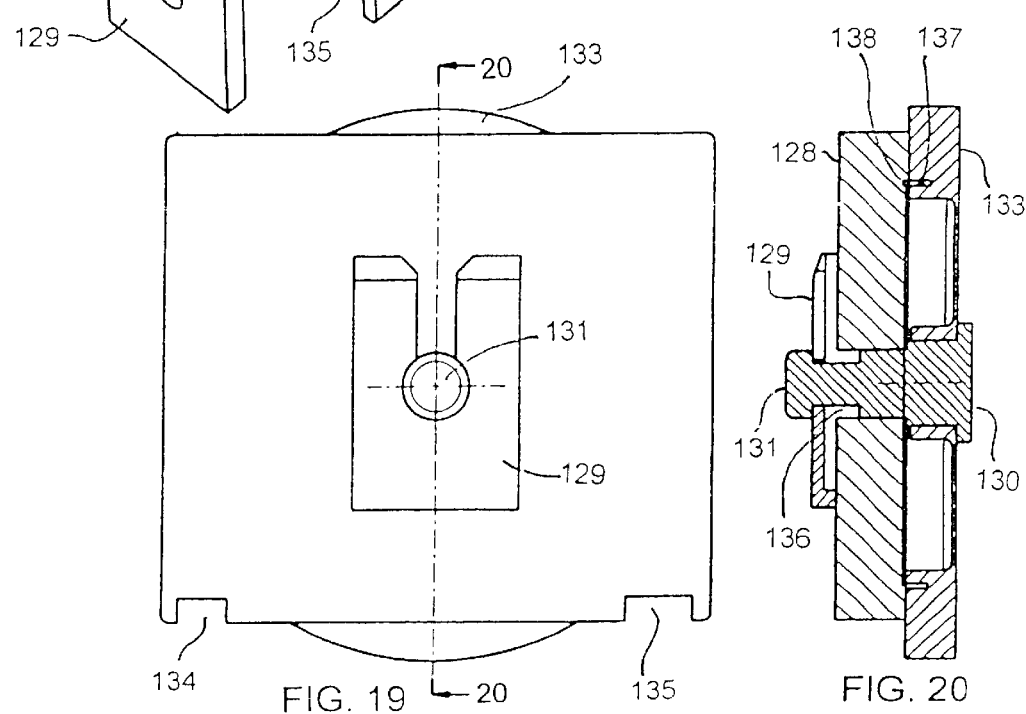
FIG. 19
FIG. 20

METHOD FOR ANALYZING AMOUNT OF ACTIVITY

This is a continuation-in-part of application Ser. No. 09/377,382 filed Aug. 19, 1999 now U.S. Pat. No. 6,454, 696.

The invention relates to a method for analyzing amount of activity due to radioactive seeds having specified nominal activities and that are to be implanted in animal tissue.

BACKGROUND OF THE INVENTION

In the field of implanting radioactive seeds in an animal body the American Association of Physisists in Medicin (AAPM) is recommending in TG 43 that of each badge of seeds used for the treatment of a patient at least 10% be independently measured. In case the seeds are to be implanted in a manual procedure the seeds are delivered to the hospital in a non-sterile form. The hospital physicist is required to measure at random 10% of the seeds delivered before sterilization to confirm the activity level of the seeds in the badge. In known automated procedures seeds are delivered in a sterile form, however, no solution has been described so far of measuring at random the seeds of a badge without breaking sterility of the sterile delivered seeds.

A device for manually implanting radioactive seeds in an animal body is known from Journal of Brachytherapy International 1998;14:21–27. Therein is described a device in which under ultrasound guidance using an ultrasound probe and using a first template implant needles, hereinafter needles, are placed in a prostate gland. Under fluoroscopy the positions of the needles are checked. For every individual needle the length of the train of seeds is determined. The trains of seeds are placed into the needles with custom-made stylets. Thereafter a second template is attached to a stepping unit in the same way as the ultrasound probe. The ends of the stylets are placed in the second template at the same positions as the needles in the first template. The correct distance between the second template and the ends of the needles is established and the needles are retracted over the stylets manually.

The described method of implanting is cumbersome in that a lot of specialized and delicate tasks have to be fulfilled manually. Acting like this it is not possible to reach a high degree of accuracy in the placement of the seeds. The determination of the desired placements of the seeds can be done with very high accuracy based upon the known physics of the radioactive radiation emitted by the seeds and the geometry of the prostate gland. Such determination of desired placement usually is done by means of a computer programmed with a known therapy planning program. One such program is marketed under the trademark PLATO by Nucletron BV of the Netherlands. Nevertheless the manual placement of the seeds makes it necessary to recheck the number of seeds introduced and if necessary to introduce additional seed trains.

U.S. Pat. No. 6,129,670 discloses an apparatus for implanting radioactive seeds in a patients' body. The seeds are present in sterilized cassettes for holding seeds and spacers. The seeds are being described as having one of two different radioactive activity levels. The apparatus comprises means for loading an implant needle with a desired train of seeds and spacers. The apparatus comprises radiation sensing means along the needle at positions where the seed or a spacer may end up when a train of seeds and spacers is being assembled. The radiation detecting means distinguish between no radiation, i.e., a spacer, a first radioactive activity level and a second radioactive activity level. After a needle has been provided with a desired train of seeds and spacers the needle is decoupled from the apparatus and inserted into a convenient storage system for the loaded needles until they are used.

The company South Bay Medical describes a Smart Cartridge which holds a number of pre-sterilized seeds together with spacers, blanks and needle packs.

Neither U.S. Pat. No. 6,129,670 nor South Bay Medical describe how to measure activity of at least 10% of the seeds in a badge without breaking sterility.

BRIEF DESCRIPTION OF THE INVENTION

It is an object of the invention to provide a method for analyzing amount of activity due to radioactive seeds having specified activities and that are to be implanted in animal tissue comprising the steps of determining a pre-plan comprising determining a desired distribution of implanted of said radioactive seeds and non-radioactive spacers in said tissue, in accordance with said pre-plan assembling trains of said radioactive and said spacers for implantation, accurately determining radiation activity of each seed while adding such seeds to said train with an accuracy that allows distinguishing between different activities within tolerance ranges of said specified activities for such seed.

It is a further object of the invention to provide a method for implanting radioactive seeds having specified activities in animal tissue comprising the steps of determining a pre-plan comprising determining a desired distribution of implanted radioactive seeds and non-radioactive spacers in said tissue, in accordance with said pre-plan assembling trains of seeds and spacers for implantation, determining radiation activity of each seed while adding such seed to a said train, implanting unloaded needles in said tissue, assembling said trains outside said implanted onloaded needles in an assembly unit, connecting said assembly unit to a said implanted unloaded needle before, during or after assembling a said train for such needle, transferring said assembled train from said assembly unit to said implanted unloaded needle and implanting said transferred assembled train in said animal tissue.

It is still a further object of the invention to provide a method for determining a postplan for radiation treatment of animal tissue, said method comprising determining a pre-plan for radiation treatment of said animal tissue based upon specified activities of to be implanted radioactive seeds, in accordance with said pre-plan assembling trains of said seeds and spacers for implantation, determining radiation activity of each seed while adding such seed to a said train and determining said postplan using determined radiation activities.

The invention shall now be described in more detail with reference to the accompanying drawings.

Further scope of the applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

The present invention will become more fully understood from the detailed description given hereinbelow and the accompanying drawings which are given by way of illustration only, and thus are not limitative of the present invention, and wherein:

BRIEF DESCRIPTION OF THE DRAWINGS

In the drawing,

FIGS. 3A and 3B show details of the device shown in FIG. 2;

FIG. 18 shows an exploded view of the pushing drive module;

FIG. 19 shows a front view of the pushing drive module;

FIG. 20 shows a view along the line 20—20 in FIG. 19;

DESCRIPTION OF PREFERRED EMBODIMENTS

It is to be noted that the following description will be made with respect to treatment of a prostate gland. However, the invention may be used in far more applications in which (radioactive) seeds are deposited in other parts of an animal body.

Figure 1:
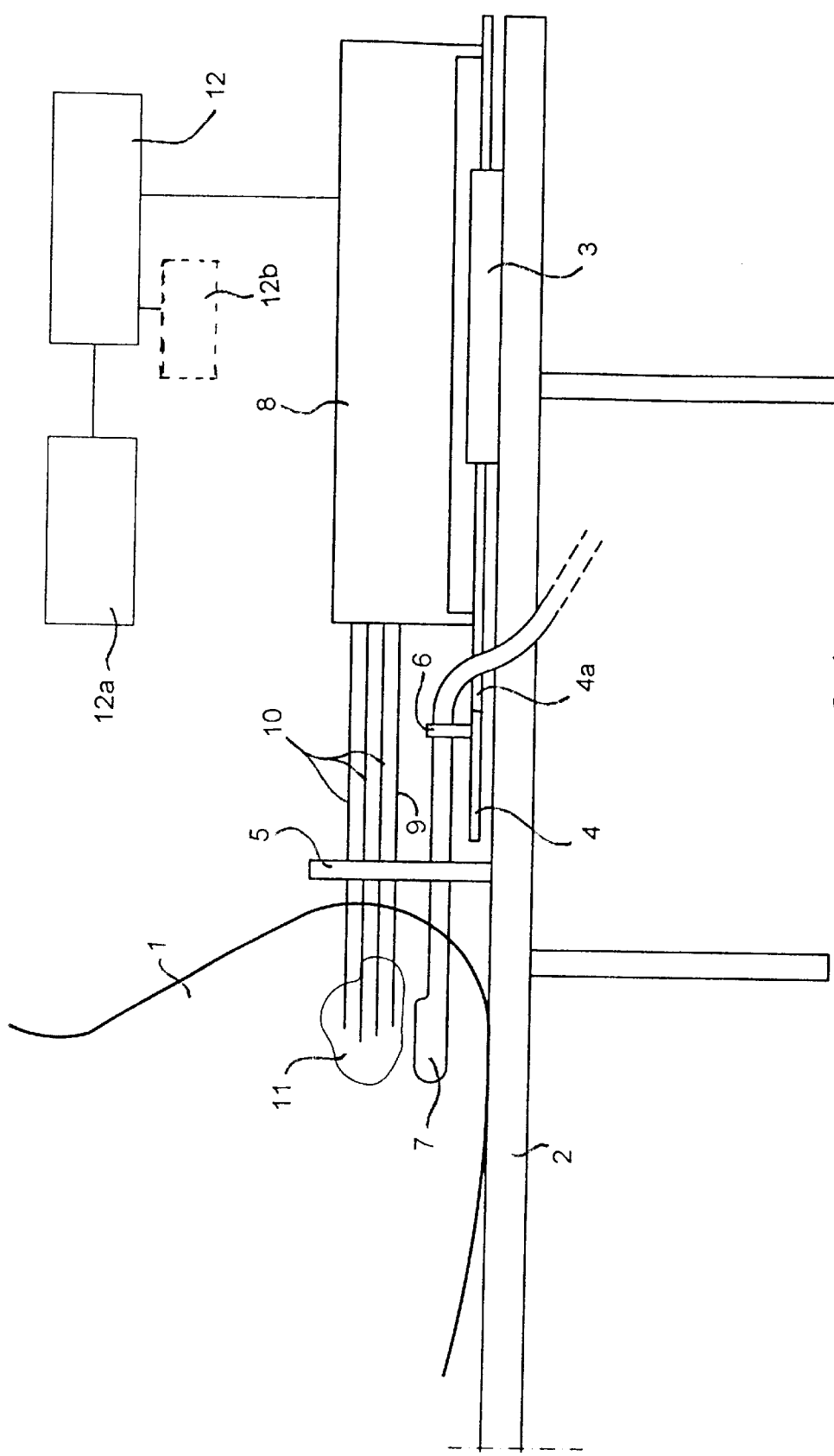
FIG. 1 shows a very schematic and simplified device according to the invention.

FIG. 1 shows in very schematic form various elements of a device for implanting radioactive seeds into a prostate gland. A patient 1 is shown lying in lithotomy position on a table 2. Fixedly connected to the table 2 is a stepper unit 3. Stepper unit 3 comprises a drive to move movable tables 4 and 4a stepwise. Connectable to table 4 is a template 5. By means of a holder 6 a transrectal ultrasound probe 7 is fixedly connectable to table 4a. A needle 9 is used for fixing the prostate gland 11 in position relative to the template 5. A number of needles 10 is fixed into position through the template 5 in the prostate gland 11. The template 5 determines the relative positions of the needles 10 in two dimensions. The needles 10 are open at their distal ends and are sealed of by a plug of biocompatible, preferably bioabsorbable wax. In a first embodiment seed loading unit 8 is connectable to the table 4. In a second embodiment seed loading unit 8 is a stand alone unit. A well-known therapy planning module 12a is provided for determining a desired distribution of implanted radioactive seeds of specified nominal activities and non-radioactive spacers. Such desired distribution determines the number and relative positions of seeds in each needle for implantation in the prostate gland 11. The result of that determination is a plan called a pre-plan. Such therapy planning module 12a usually comprises a computer programmed with a therapy planning program. One such a therapy planning program is marketed under the trademark PLATO by Nucletron BV of the Netherlands. Other such programs are also known. The therapy planning module 12a is connected to the seed loading unit 8 through a control device 12 for controlling the number of seeds for each needle. Control device 12 may be a separate device or may be an integrated part either of the seed loading unit 8 or of the therapy planning module 12a or may be embodied in the software of the therapy planning module 12a or of the seed loading unit 8. In one embodiment control device 12 comprises a programmed microprocessor, preferably a 16-bit version. Such a microprocessor may be a Siemens 166 or a Philips 8051 EA or one of another manufacturer.

Operation of the device shown in FIG. 1. A patient 1 is under spinal or general anesthesia and lying on the operating table 2 in lithotomy position. Trans-rectal ultrasound probe 7 is introduced into the rectum and the probe is connected to the stepper unit 3 and table 4 through holder 6. On an image screen, well known, an image may be seen of the inside of the patient in particular of the prostate gland 11 as seen from the point of view of the ultrasound probe 7. The template 5 is attached to the stepper unit 3. Thereby the correlation of the ultrasound image geometry and the template 5 is guaranteed. The prostate gland 11 is fixed relative to the template and the stepper unit 3 and the ultrasound probe by means of one or more needles 10. Subsequently further needles 10 are introduced in the body and the prostate gland under ultrasound guidance one by one. Moving the ultrasound probe with the stepper unit 3 longitudinally within the rectum controls the needle depths. After all needles 10 have been placed their positions relative to the prostate gland 11 are determined in at least one of several known ways. In a known way the therapy planning module 12a determines how the needles 10 are to be placed in the prostate and how many radioactive seeds are to be placed in what order in each of the needles 10 (the pre-plan). The information about the desired placement of the radioactive seeds in the needles 10 is used to control the seed loading unit 8. Usually the seeds are spaced from each other by spacers. For example seeds of 1 cm length may be spaced by spacers also of 1 cm length. Other measures of seeds and spacers are imaginable.

A set of seeds and spacers loaded or to be loaded into a needle will be called a seed train or a train of seeds or a seed-spacer train. For each needle 10 the configuration of an applicable seed-spacer train is determined by the therapy planning module 12a. The seed loading unit 8 is controlled by the control device 12 to make up a seed-spacer train for each needle 10. The making up of a specific seed-spacer train in accordance with the pre-plan will be described hereinbelow later on. Once a seed-spacer train is to be, is being or has been made up for a specific needle a connection is made to the specific needle. After the seed-spacer train has been made up it is urged into the specific needle by a pushing drive that is part of the seed loading unit 8. Since all elements of the seed loading unit 8 and the needles 10 and their interconnections are of specific pre-known dimensions, which may or may not be the same for all like elements and such dimensions have been made known, e.g. pre-loaded in or pre-entered via a keyboard 12b to the control device 12 the pushing drive pushes with a pushing wire the seed-spacer train just until it reaches the distal end of the specific needle. Subsequently the pushing wire is fixed in position and the specific needle is retracted over a distance equal to or slightly greater than the length of the seed-spacer train in it. Thereby the wax plug and the seed-spacer train are introduced in the prostate gland 11. Next the pushing wire is withdrawn into the seed loading unit 8 for pushing a next seed-spacer train into the prostate gland 11. The delivery of seed-spacer trains in the prostate gland continues until each needle 10 has been retracted and a number of seed-spacer trains equal to the number of needles 10 has been delivered in the prostate gland 11. Subsequently the seed loading unit 8 is disconnected from the stepper unit 3 and the needles 10 are retracted from the patient completely. After the geometry of the implanted seeds has been checked under fluoroscopy or another method of checking the presence of the seeds in the prostate gland 11, i.e. after determination of actual locations of implanted seeds and after removal of the ultrasound probe 7 the patient 1 is hospitalized for recovery.

Figure 2:
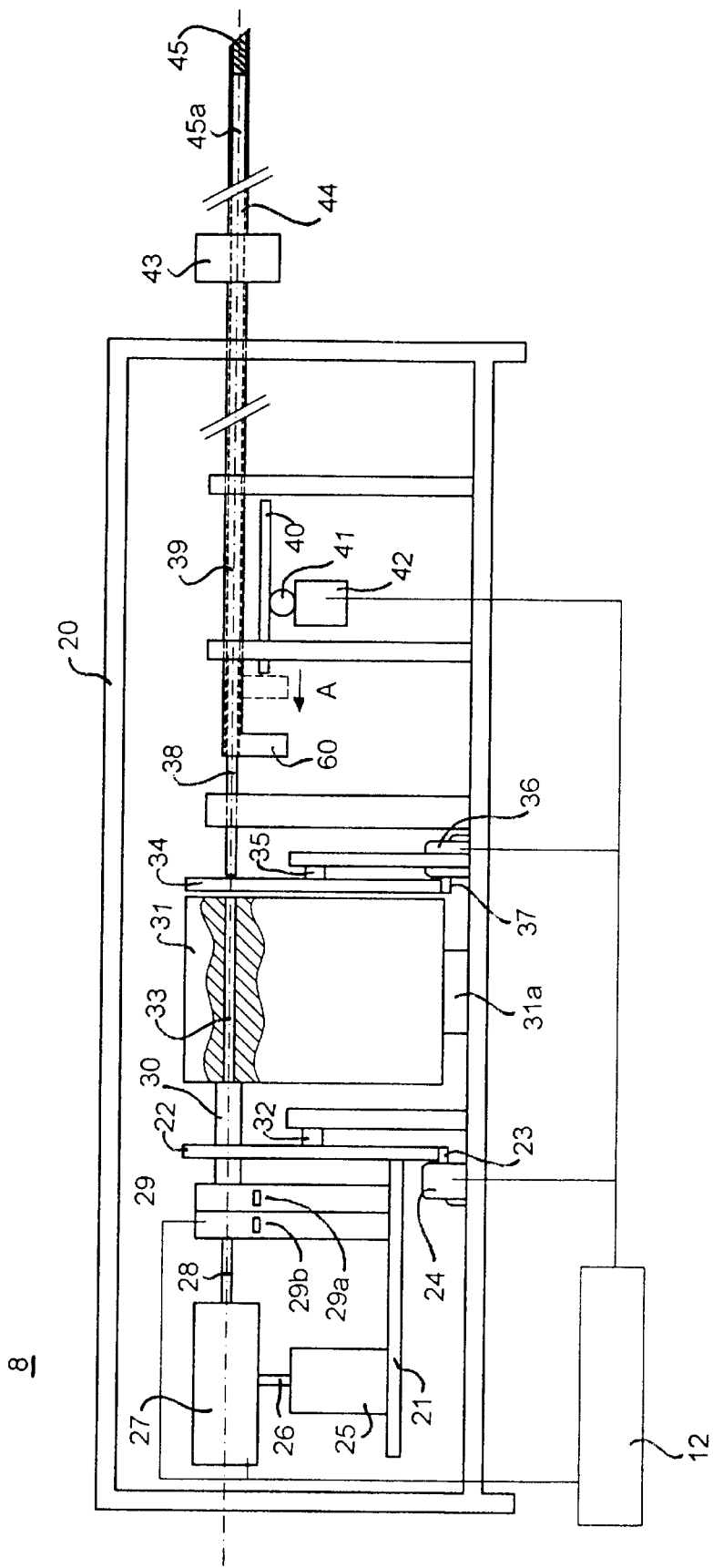
FIG. 2 shows a schematic view of an embodiment of a first device according to the invention.

FIG. 2 shows a schematic representation of a first embodiment of a seed loading device 8 according to the invention.

Inside a housing 20 there is provided a platform 21. The platform 21 is fixed to a wheel 22. Along the rim of the wheel 22 teeth are present that mesh with teeth on a shaft 23. Toothed wheel 22 is rotatable about a shaft 32. Shaft 23 is driveable by a motor 24. On the platform 21 a motor 25 is placed. A shaft 26 of motor 25 connects detachably to a pushing drive 27. The pushing drive 27 connects through a tube 28 to seed and spacer supply container 29. Supply container 29 is detachably fixed to platform 21. A seed and a spacer are indicated schematically as 29a and 29b respectively. Supply container 29 comprises a channel 59, shown in FIGS. 3A and 3B that is longitudinally aligned with tube 28. Fixed to the supply container 29 is a further tube 30 that is longitudinally aligned to the channel 59 in supply container 29. Tube 30 fits through a corresponding opening in wheel 22 and stretches until it reaches multichannel holder 31. Multichannel holder 31 is detachably fixed in housing 20 and supported by a support element 31a. Multichannel holder 31 comprises a number of bores one of which is shown as 33. The bores in multichannel holder 31 are arranged in circular order such that upon rotation of wheel 22 tube 30 sequentially aligns with the bores in multichannel holder 31. A plate 34 includes a number of openings. The openings in plate 34 are also arranged in circular order. Plate 34 is switchable between a first and a second position about shaft 35 by means of a motor 36 and a shaft 37. Instead of a motor 36 and shaft 37 also an electromagnet (not shown) may be used to switch plate 34 from its first to its second position and vice versa. Shaft 37 meshes with teeth on the circumference of plate 34. In the first position the openings in plate 34 coincide with the bores 33. In the second position all bores 33 are closed of by plate 34. Longitudinally aligned with bore 33 is a tube 38. Tube 38 fits slideably inside a needle retraction tube 39. A distal end of tube 38 is inside tube 39. tube 39 is in longitudinal alignment with bore 45a in needle 44. Needle retraction tube 39 is movable back and forth between a first and a second position. The first position is shown in phantom whereas the second position in shown in drawn lines in FIG. 2. A needle retraction mechanism is shown schematically as comprising a toothed bracket 40, a toothed wheel 41 and a drive 42 for the toothed wheel 41. Retraction tube 39 extends through the housing 20 and ends in a coupling 43. Coupling 43 couples retraction tube 39 to a needle 44. Needle 44 at its distal end is shown provided with a plug of wax 45. Housing 20 is provided with appropriate closeable openings (not shown) for installing pushing drives 27, supply containers 29, multichannel holders 31 and tubes 38. Housing 20 is provided with a number of tubes 38, retraction tubes 39, toothed brackets 40, toothed wheels 41 and drives 42 for the toothed wheels 41 which number is equal to the number of channels 33 in multichannel holder 31.

Before starting to use seed loading unit 8 pushing drive 27 is installed on shaft 26. Also installed before use are supply container 29 with tube 30, a multichannel holder 31 and a tube 38 with corresponding coupling 43. Pushing drive 27, supply container 29, tube 30, multichannel holder 31, tube 38 coupling 43 and needle 44 all are sterilized before being used and installed. Under control of the control device 12 the channels 33 in the multichannel holder 31 are filled with appropriate seed-spacer trains. Filling of the channels 33 is done by first loading a seed 49 and a spacer 48 into channel 59 in the supply container 29. Subsequently a pushing wire present in the pushing drive 27 is moved by motor 25 to push the spacer-seed set present in channel 59 through tube 30 into channel 33. It may be noted that a spacer seed set may also consist of only a spacer or only a seed depending on the required radiation distribution as determined by the therapy planning module 12a. Plate 34 has been switched under control of control device 12 meanwhile such that the openings therein do not coincide with the channels 33 in multichannel holder 31. A plurality of needles 44, i.e. a first one, a second one, a third one, a fourth one etc. has been introduced into the body and has been connected through corresponding first, second, third, fourth etc. couplings 43 to corresponding first, second, third, fourth etc. tubes 39 respectively. Once all seed-spacer trains have been set up in the channels 33 wheel 22 is rotated to bring tube 30 in longitudinal alignment with a first one of the channels 33 which is in longitudinal alignment with a first one of the tubes 38 which is connected through a first tube 39 and a first coupling 43 to a first needle 44. Channel 59 now is free of any seeds and spacers. Under control of the control device 12 the pushing wire of pushing drive 27 enters tube 28, channel 59, tube 30, first channel 33 and pushes forward the seed-spacer train out of the first channel 33 into the first tube 38 and further through the first coupling 43 into the first needle 44 until it reaches the plug of wax 45 in the first needle. The pushing wire is fixed in position then whereby the first seed-spacer train remains fixed between plug 45 and the distal end of the pushing wire. After that first motor 42 is activated to turn first wheel 41 and thereby move first bracket 40 in the direction of arrow A in FIG. 2. First bracket 40 pushes against first arm 60 of first retraction tube 39.

Thereby first retraction tube 39 is moved in the direction of arrow A in FIG. 2. Since first retraction tube 39 is connected to first needle 44 that first needle 44 is retracted in the direction of arrow A. As a consequence the plug of wax and the first seed-spacer train are introduced in the prostate gland 11. Then the pushing wire is retracted at least as far as the point at which the distal end has entered the tube 30. Then the wheel 22 is rotated for the tube 30 to come into longitudinal alignment with a second channel 33 with a second seed-spacer train in it. Then the whole series of actions described hereinbefore with respect to the first seed-spacer train takes place with respect to the second seed-spacer train. Thereafter all steps are repeated for a third, fourth etc. seed-spacer train until all seed-spacer trains present in channels 33 have been introduced in the prostate gland 11.

It is to be noted that needle 44 is an open needle. As a consequence blood may have entered bore 45a and have come into contact with the pushing wire. Various parts may have been contaminated with blood by the pushing wire such as the coupling 43, the tube 38, the channels 33, the tube 30, the supply container 29, the tube 28 and the pushing drive 27. It may also be that blood has passed past the pushing wire into the bore 46, the coupling 43, the tube 38, the channels 33, the tube 30, the supply container 29, the tube 28 and the pushing drive 27. Due to the modular build up of the seed loading unit 8 after of all the seed-spacer trains have been delivered all the elements mentioned that might have been contaminated with blood can be taken out of the seed loading unit 8 either for sterilization or for disposal, as appropriate.

FIGS. 3A and 3B show in schematic and simplified form a module comprising a supply container 29 in front view and in side view respectively. Supply container 29 comprises two reservoirs 46 and 47 respectively. Reservoir 46 is for spacers 48 and reservoir 47 is for seeds 49. For clarity only limited numbers of spacers 48 and seeds 49 are shown. In practice several tens of spacers and seeds are present in reservoirs 46 and 47 respectively.

The reservoirs 46 and 47 comprise springs 50 and 51 and plungers 52 and 53 respectively. Shown for the spacers 48 is a drive 54. Drive 54 is arranged upon activation to push member 55 in the direction of the arrow 56 against the force exerted by a spring 57. Thereby an opening 58 comes in line with reservoir 46 thereby allowing a spacer 48 to enter channel 59. Indicated by corresponding reference numerals but not shown is a same mechanism 54a, 55a, 56a, 57a and 58a attached to reservoir 47 for making a seed 49 enter channel 59.

In operation supply container 29 while outside the housing 20 is filled under sterile conditions with seeds and spacers in reservoirs 46 and 47. Thereafter a filled supply container 29 is placed in the seed loading unit 8. Fixedly connected to housing 20 are drives 54 and 54a. Upon placement of supply container 29 push members 55 and 55a come into contact with drives 54 and 54a respectively. The position of push member 55 shown in FIG. 3A is the rest position. In case a spacer/seed has to be added to the seed-spacer train that is being configured under control of control device 12 drive 54/54a is activated to push push member 55/55a against the force of spring 57/57a such that opening 58/58a opens up channel 59 to the spacer/seed 61/61a on top of the stack. Under the force of spring 50/51 the spacer/seed 61/61a on top of the stack is pushed into channel 59. Thereafter the drive 54/54a is deactivated whereby spring 57/57a pushes push member 55/55a back to its rest position. The spacer/seed 61/61a may now be pushed into channel 33 of the multichannel holder 31 by means of the push wire of push drive 27. After retraction of the push wire of the push drive 27 channel 59 is free to receive a next spacer/seed.

Figure 4A:
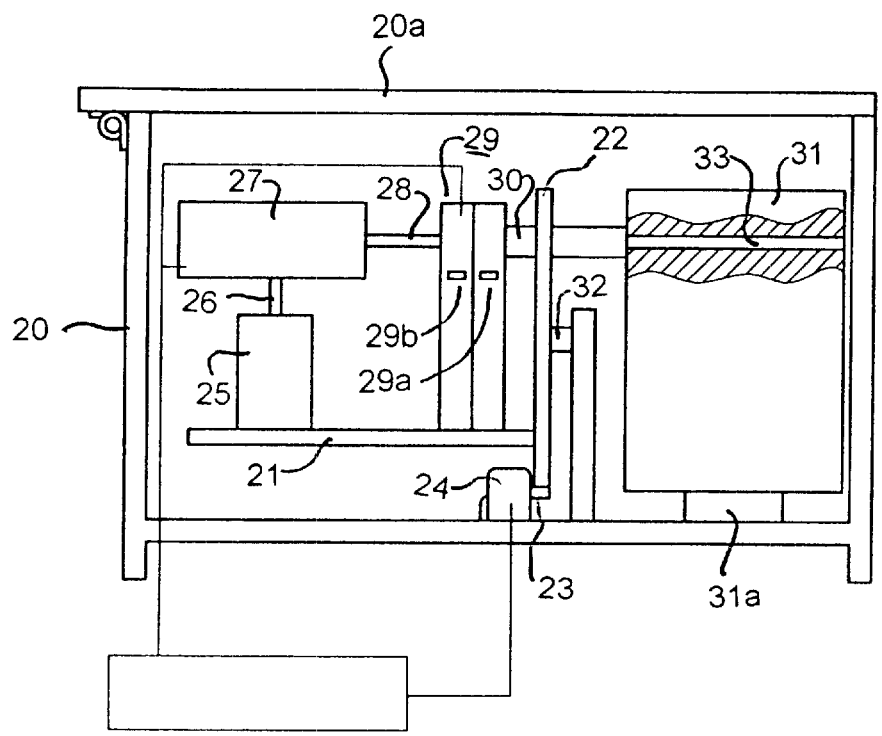
FIG. 4A shows a schematic view of a first embodiment of a seed loading module.
Figure 4B:
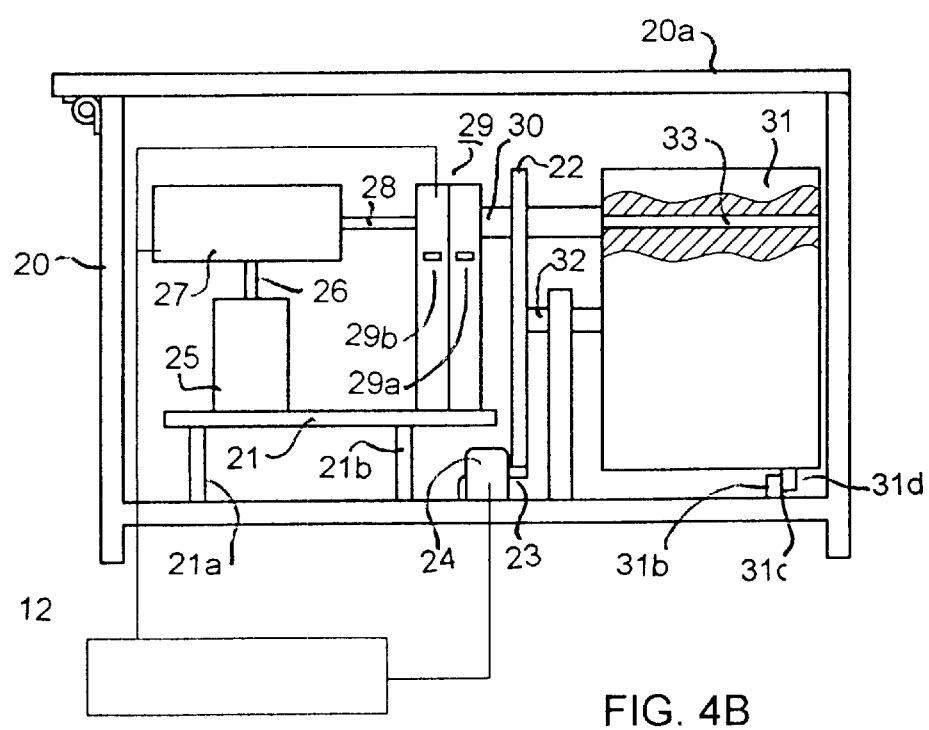
FIG. 4B shows a schematic view of a second embodiment of a seed loading module.
Figure 5:
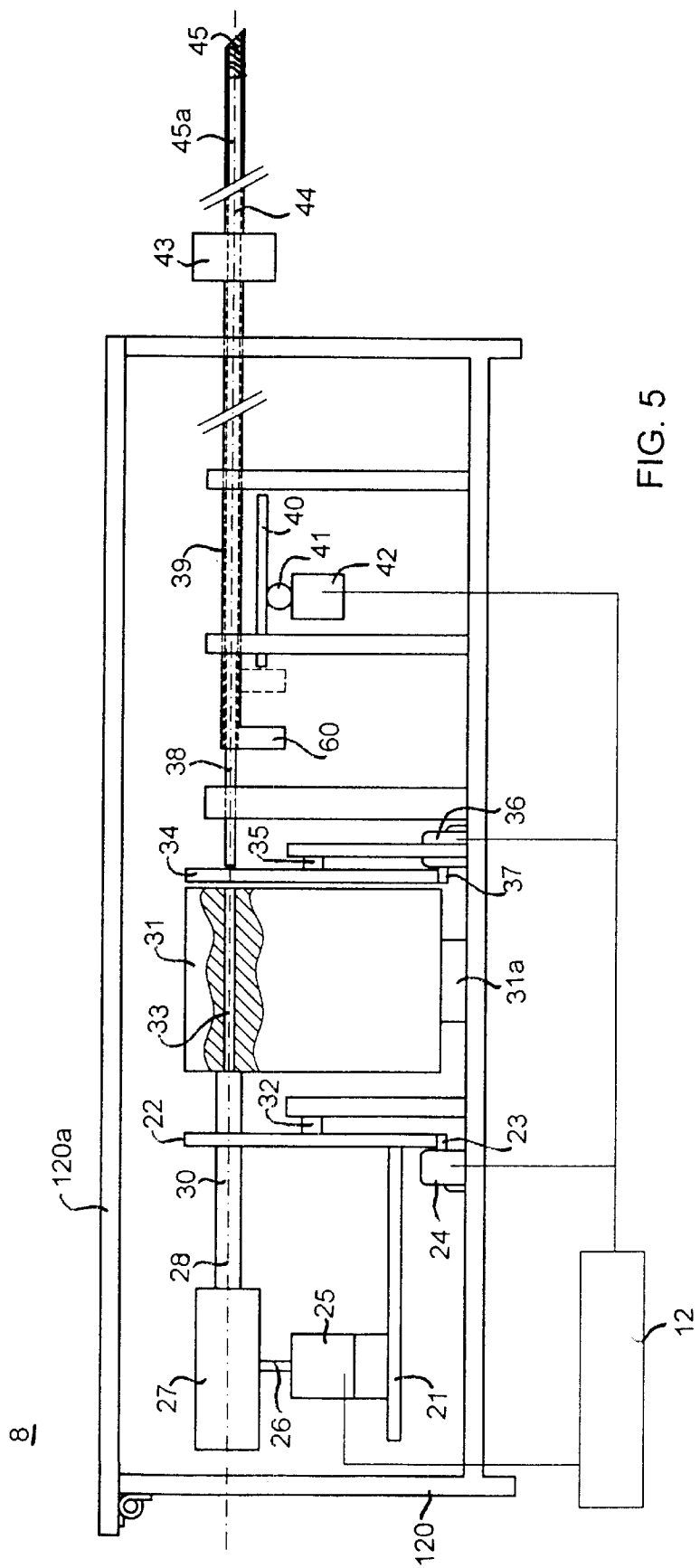
FIG. 5 shows a schematic view of a first embodiment of a seed implanting module.

FIGS. 4A, 4B and 5 show two embodiments of a seed loading module and an embodiment of a seed implanting module as modular parts of a device according to the invention. In that embodiment a spatial division has been made between a module dedicated to loading a multichannel holder 31 with seed-spacer trains and a module dedicated to implanting the seed-spacer trains from the multichannel holder 31 in the body.

In FIGS. 4A, 4B and 5 like elements have been identified by the same reference numerals, which reference numerals also are identical to those used in FIG. 2 for like elements.

In FIG. 4A housing 20 is equipped with a hinged cover 20a allowing easy replacement of supply container 29 and multichannel holder 31. Multichannel holder 31 is filled with seed-spacer trains in like manner as described in relation to FIG. 2. After all relevant channels 33 in multichannel holder 31 have been filled with appropriate seed-spacer trains cover 20a is opened thereby giving access to multichannel holder 31 for evacuation thereof and placement in a device as to be described hereinbelow with reference to FIG. 5.

In FIG. 4B platform 21 is fixedly mounted to housing 20. Toothed wheel 22 is rotatable on shaft 32. The teeth of wheel 22 mesh with teeth of a shaft 23 that is rotatable by a motor 24. Wheel 22 is provided with an opening such that tube 30 extends uninterruptedly up until multichannel holder 31. Due to the presence of the opening wheel 22 may be rotated without breaking the tube 30. Multichannel holder 31 is provided with a central opening meshing with shaft 32 upon insertion of multichannel holder 31 through opened hinged cover 20a. For better stability of multichannel holder 31 one or more support wheels 31d on shafts 31c supported by shaft support elements 31b may be present.

Since supply container 29 now is fixed relative to housing 20 multichannel holder 31 is rotated by motor 24 through shaft 23 and wheel 22 and shaft 32 to place a channel 33 in longitudinal alignment with tube 30. As has been described hereinbefore in relation to FIG. 2 seed-spacer trains are made up in channels 33 of multichannel holder 31. Each time a channel 33 has been filled with an appropriate seed-spacer train motor 24 is activated to rotate multichannel holder 31 until the next channel 33 to be filled is in longitudinal alignment with tube 30. After all relevant channels 33 in multichannel holder 31 have been filled with appropriate seed-spacer trains cover 20a is opened thereby giving access to multichannel holder 31 for evacuation thereof and placement in a device as to be described hereinbelow with respect to FIG. 5.

FIG. 5 shows a seed implanting module as it may be used with a multichannel holder 31 according to one of FIGS. 4A and 4B. FIG. 5 is almost identical to FIG. 2, though supply container 29 is not present and tubes 28 and 30 are merged together into a single tube. The housing 120 is provided with a hinged cover 120a. In operation of the device shown in FIG. 5 the hinged cover 120a is opened to give access to its inner space. A multichannel holder 31 provided with channels 33 loaded with appropriate seed-spacer trains may then be brought into the position shown in FIG. 5. After multichannel holder 31 has been brought into position hinged cover 20a is closed and motor 36 is operated to turn wheel 34 such that the openings in wheels 34 are in alignment with the channels 33 of the multichannel holder 31. Reference is had to the description in relation to FIG. 2 regarding to operation of the device.

Figure 6:
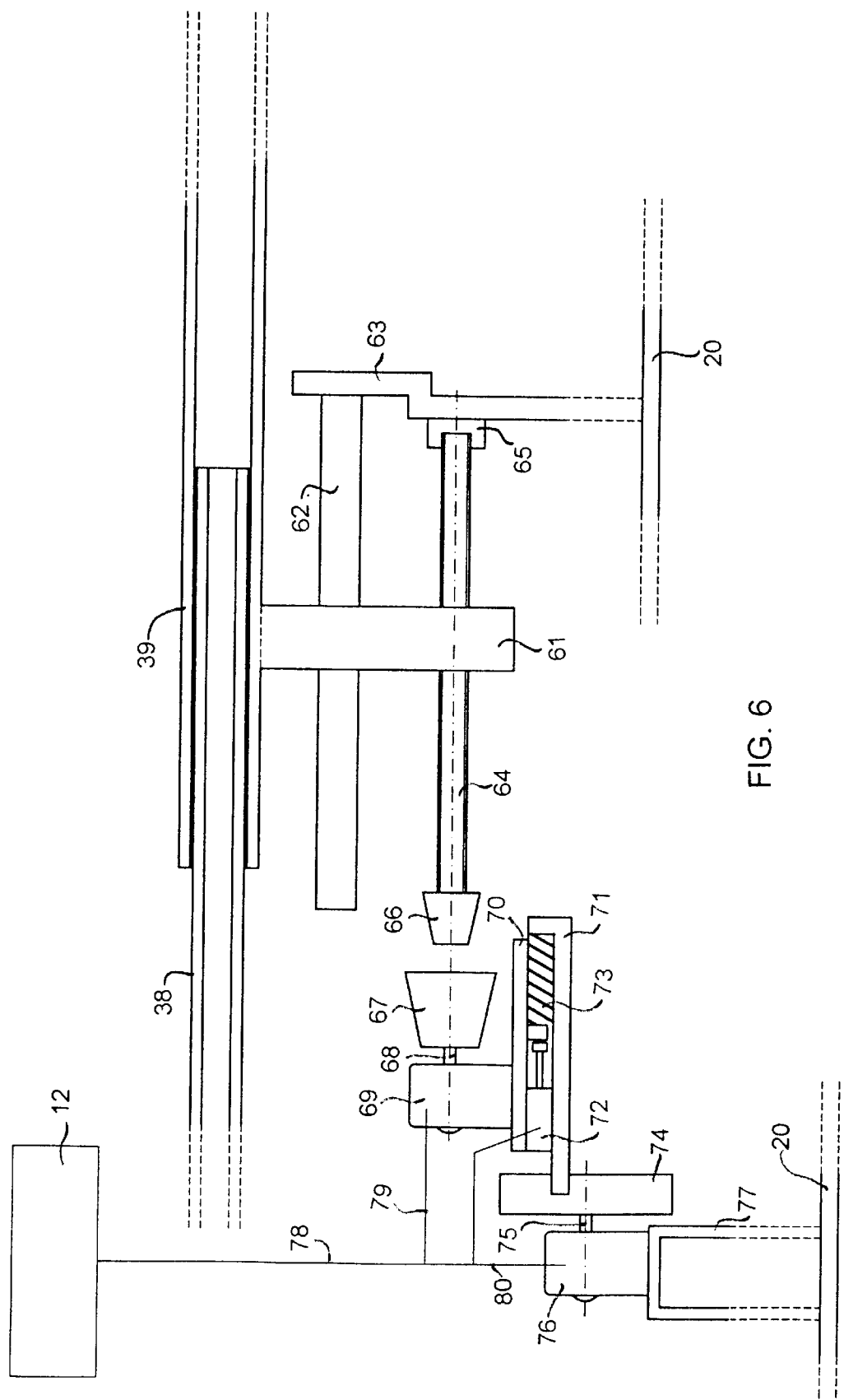
FIG. 6 shows a first embodiment of means for retracting a needle.

FIG. 6 shows a first embodiment of a means for retracting tube 39. An element 61 is fixedly connected to tube 39. Element 61 is slideably arranged over bar 62. In parallel to tube 39 bar 62 is fixedly mounted to housing 20 as schematically illustrated by bracket 63. Element 61 is provided with a hole (not shown) with screw-thread. Spindle 64 passes through the hole with screw-thread in element 61. One end of spindle 64 is connected to bearing 65. Bearing 65 is fixedly mounted on bracket 63. The other end of spindle 64 is provided with a conically shaped gear-wheel 66. Axially alignable with gear-wheel 66 is a conically shaped counter gear-wheel 67. Gear-wheel 67 is mounted on shaft 68 of motor 69. Motor 69 is mounted on movable platform 70. Movable platform 70 is movably mounted on platform 71. Platform 71 is provided with an electromagnet 72 and a spring 73. Platform 70 is in contact both with electromagnet 72 and with spring 73. Platform 71 is mounted on disk 74. Disk 74 is mounted on shaft 75 of motor 76. Motor 76 is fixedly mounted relative to housing 20 as has been schematically shown in FIG. 6 through bracket 77. Motors 69 and 76 are electronically controlled by electronic control device 12 as shown by connections 78, 79 and 80.

In order to move tube 39 either to the left or to the right in FIG. 6 motor 76 is controlled to rotate shaft 75 and thereby platform 71 such that counter gear-wheel 67 is opposite gear-wheel 66. Subsequently electromagnet 72 is energized thereby moving platform 70 with motor 69 to the right in FIG. 6. Thereby counter gear-wheel 67 meshes with gear-wheel 66. Then motor 69 is energized to rotate shaft 68, counter gear-wheel 67 a, gear-wheel 66 and spindle 64. Depending on the energization of motor 69 spindle 64 rotates in one direction or the other direction. Consequently element 61 and tube 39 move either to the left or to the right as desired.

Figure 7:
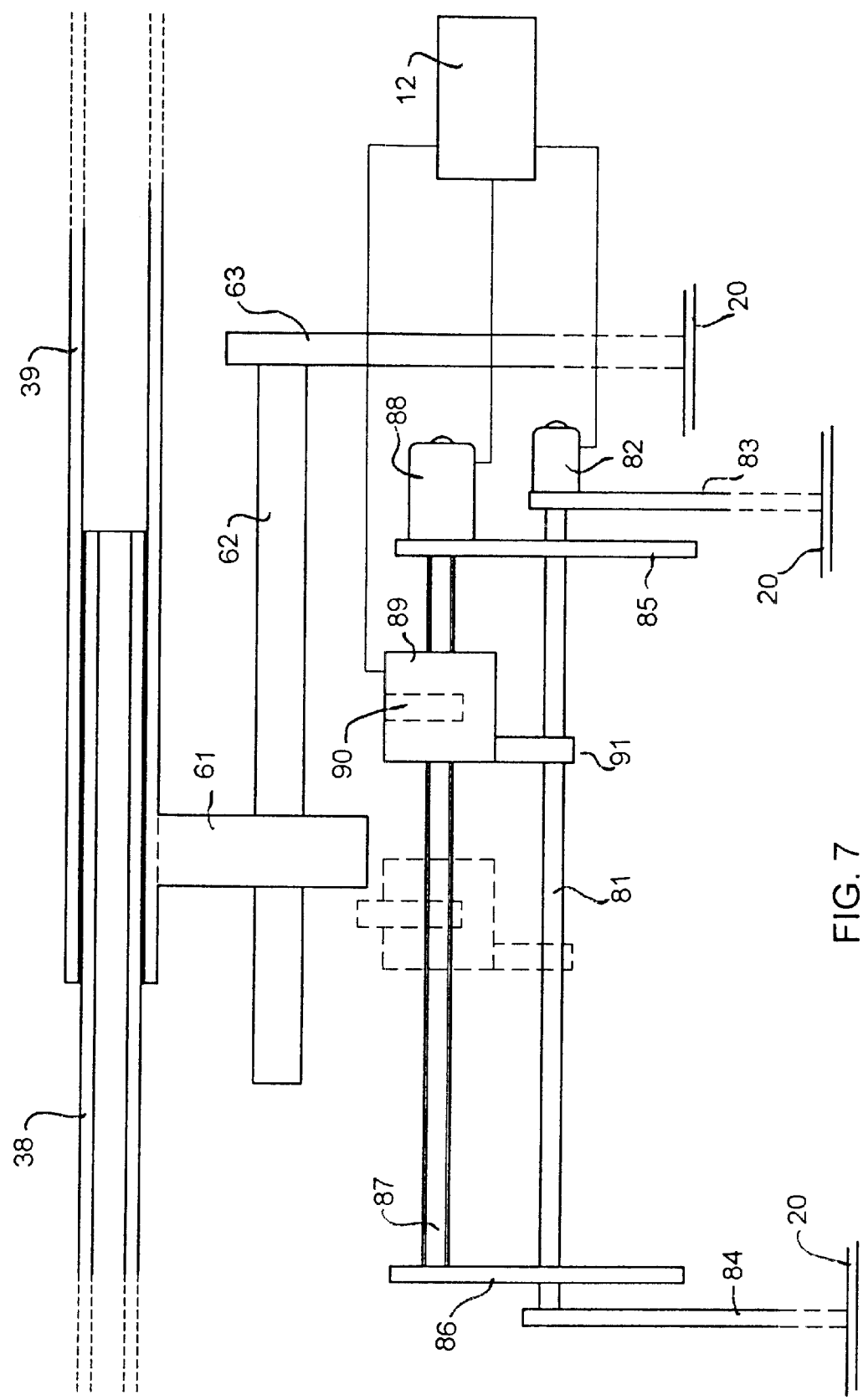
FIG. 7 shows a second embodiment of means for retracting a needle.

FIG. 7 shows a second exemplary embodiment of a means for retracting tube 39. As in FIG. 6 an element 61 is fixedly connected to tube 39. Element 61 is slideably arranged over a bar 62. In parallel to tube 39 bar 62 is fixedly mounted to housing 20 as schematically illustrated by bracket 63. A shaft 81 of a motor 82 is mounted fixedly relative to the housing 20 as indicated by brackets 83 and 84. Mounted on shaft 81 for rotation therewith are disks 85 and 86. Mounted between disks 85 and 86 and in parallel therewith is a spindle 87. Disk 86 is provided with a bearing for spindle 87 whereas disk 85 is provided with an appropriate opening therein such that spindle 87 may be connected to a motor 88 for rotation upon energization of motor 88. Mounted on spindle 88 is an electromagnet 89 with a movable core 90. The core 90 is driveable between an OUT and an IN position upon appropriate energization of electromagnet 89. Electromagnet 89 is provided with an element 91 that fits about shaft 81 in order to prevent electromagnet 89 from rotating about spindle 87 upon energization of motor 88. Motors 82 and 88 and electromagnet 89 are electronically controlled by electronic control 12.

In order to move tube 39 either to the left or to the right in FIG. 7 motor 82 it controlled to rotate shaft 81 and disks 85 and 86 with motor 88 and spindle 87 and electromagnet 89 in an appropriate position. In the IN position of core 90 electromagnet 89 may move freely relative to element 61. In the OUT position of core 90 that core 90 engages element 61 when electromagnet 89 is moved in the direction of element 61. During rotation of shaft 81 by motor 82 electromagnet 89 is controlled by electronic control device 12 such that core 90 is in the IN position. After motor 82 has rotated shaft 81 such that the desired tube 39 with its element 61 may be engaged by core 90 motor 82 is de-energized and motor 88 is energized (if necessary) to rotate spindle 87 to move electromagnet 89 to the appropriate side of element 61. When tube 39 is to be moved to the right the appropriate side of element 61 is the left side and vice versa. Next electromagnet 89 is energized whereby core 90 is moved to the OUT position and subsequently motor 88 is energized to move electromagnet 89 into engagement with element 61. This situation is shown in phantom in FIG. 7. Upon continuation of the energization of motor 88 electromagnet 89 moves on and core 90 pushes against element 61. Element 61 and tube 39 are hereby moved in the same direction and over the same distance as electromagnet 89. After tube 39 has reached a desired new position electromagnet 89 is de-energized and core 90 is retracted thereby in the IN position and out of reach of element 61. Shaft 81 may now be rotated to a new position by motor 82 such that in that new position another tube 39 may be moved.

Figure 8:
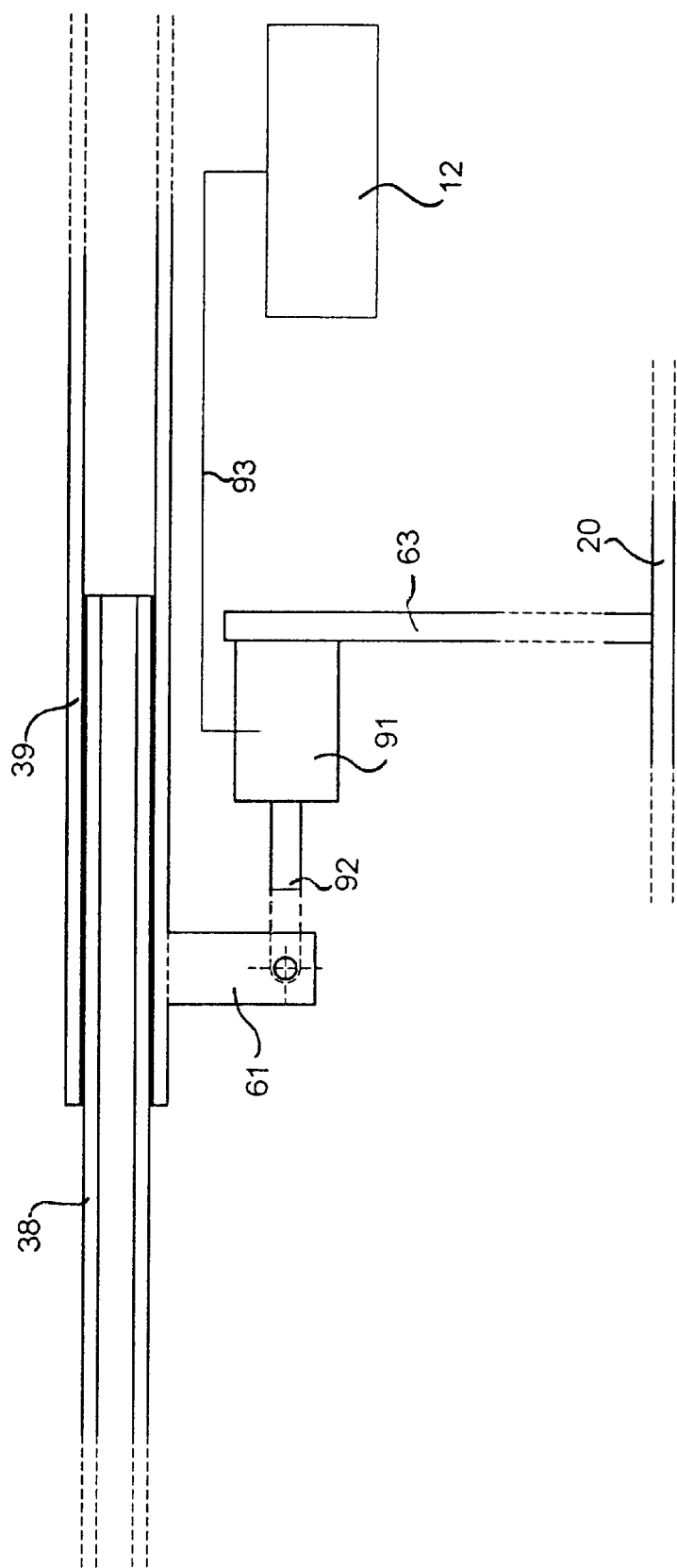
FIG. 8 shows a third embodiment of means for retracting a needle.

FIG. 8 shows a quite simple third embodiment of means for moving tube 39. As in FIGS. 6 and 7 tube 39 is provided with an element 61. A hydraulic or pneumatic cylinder 91 is mounted near element 61 on a bracket 63 which bracket is fixedly mounted relative to housing 20. Cylinder 91 has a piston 92 that may move leftward in FIG. 8. Cylinder 91 is electrically controllable by electronic control device 12 through cable 93. Cylinder 91 may be a one way or a two way device. In case it is a one way device piston 92 is kept in an OUT position for as long as cylinder 91 is energized. After de-energization of cylinder 91 piston 92 returns to an IN position. In case it is a two way device upon a first energization the piston 92 moves to an OUT (or IN) position and remains there also after de-energization. Only upon a second energization the piston moves to the IN (or OUT) position again. In case of a two way device piston 92 may be connected to element 61 as shown in phantom in FIG. 8.

The number of cylinders 91 may be the same as the number of possible tubes 39. Of course it is also possible to mount a single cylinder 91 on a rotatable disk such as used in the devices shown in FIGS. 6 and 7.

Figure 9:
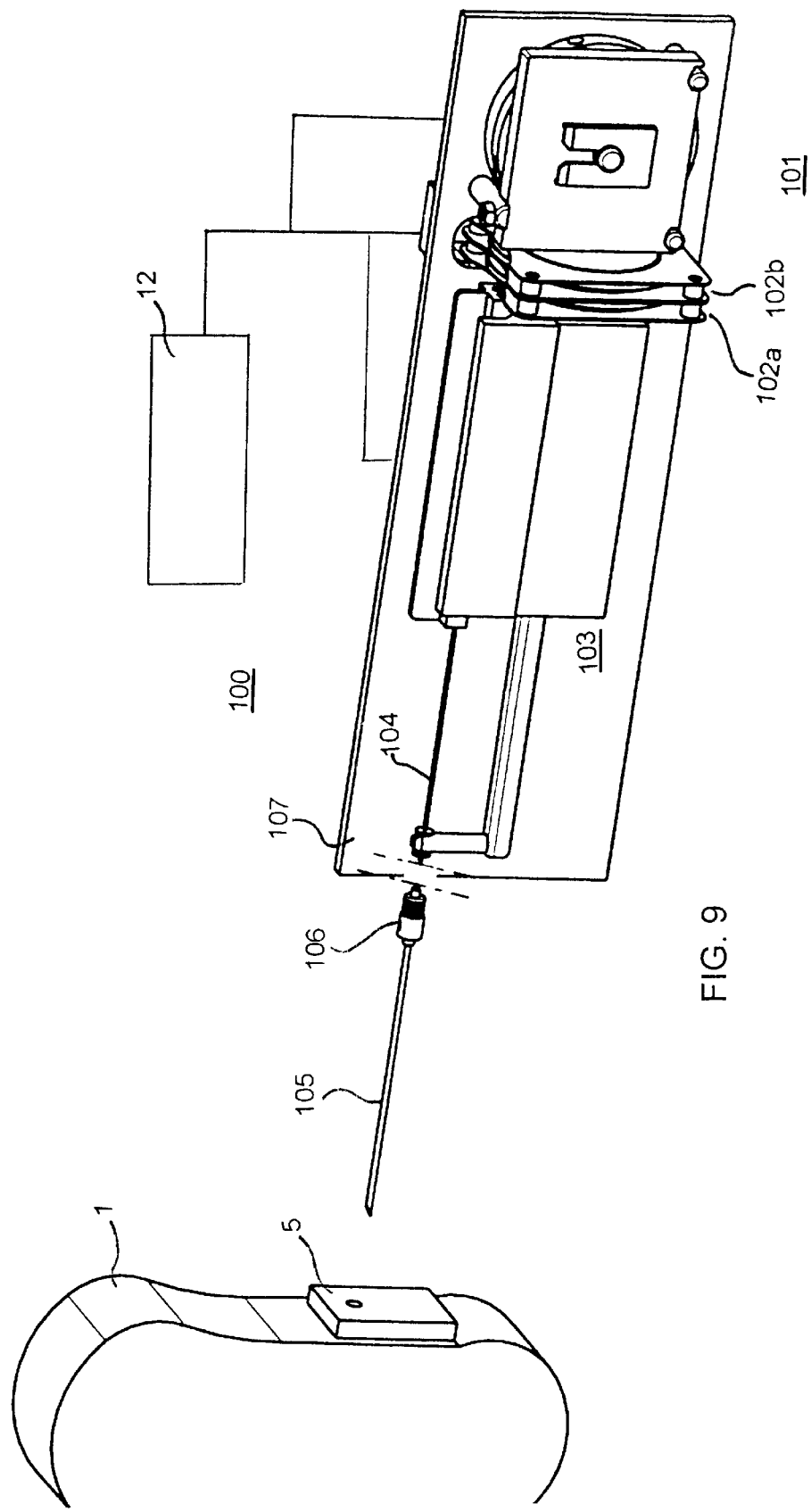
FIG. 9 shows an embodiment of another device according to the invention.
Figure 13:
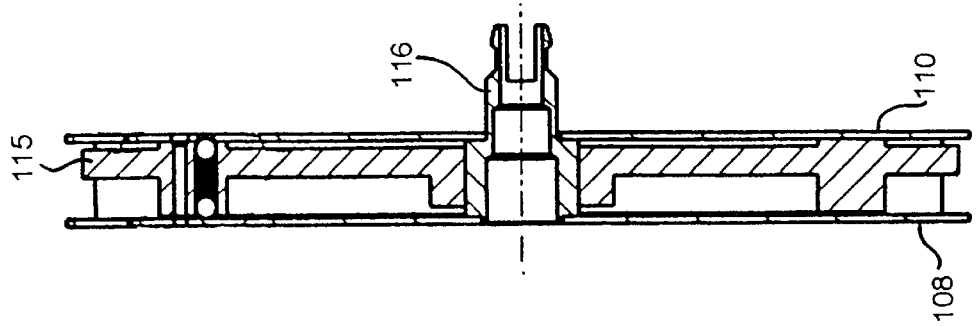
FIG. 13 shows a view along the line 13—13 in FIG. 12.
Figure 10:
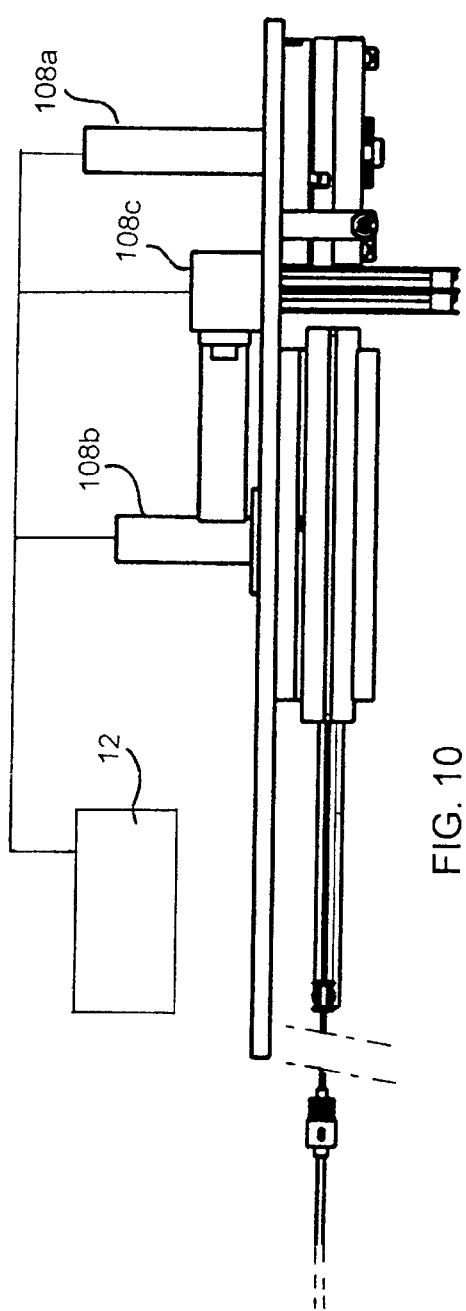
FIG. 10 shows a top view of a device as shown in FIG. 9.
Figure 11:
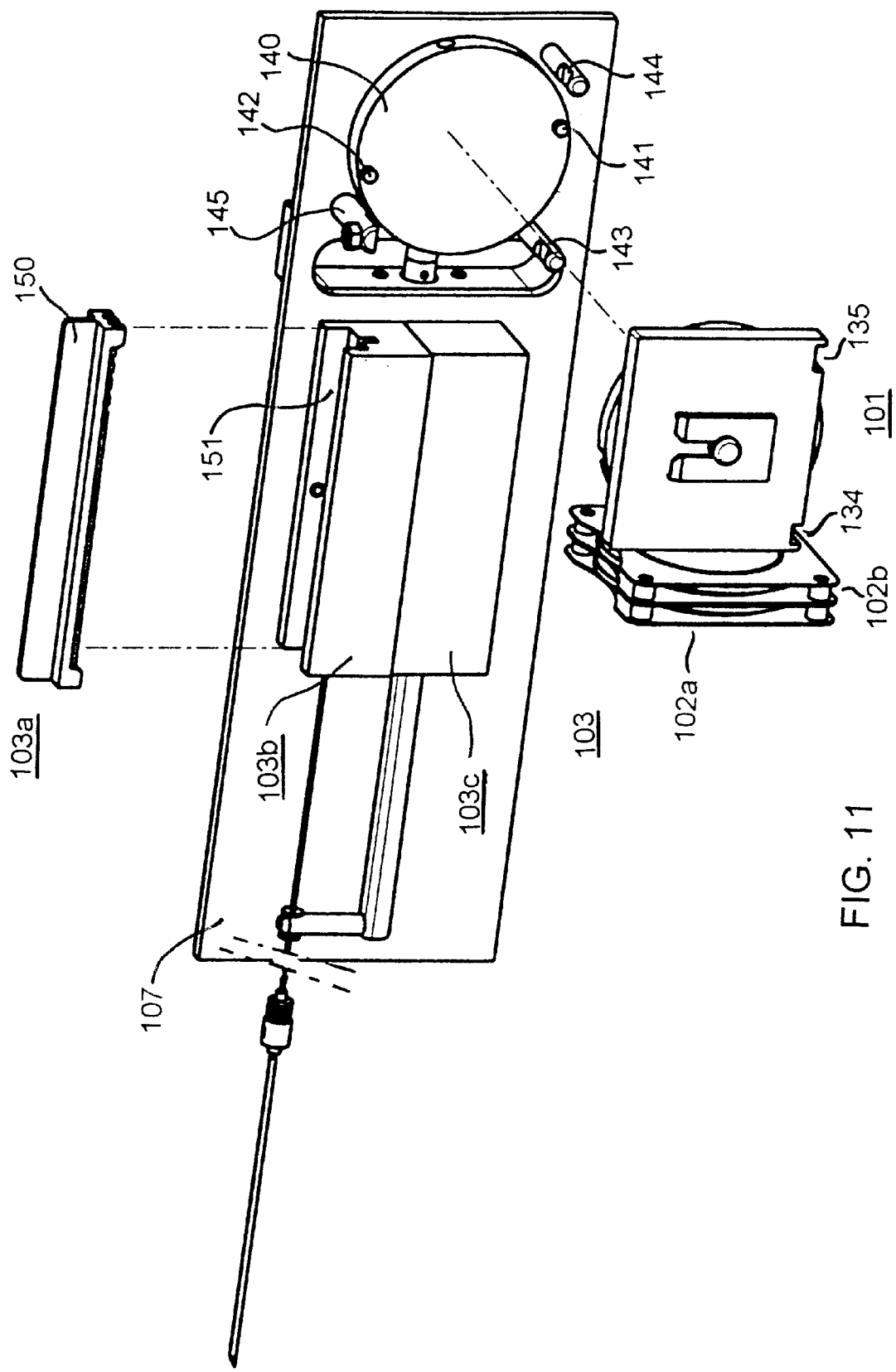
FIG. 11 shows a view of various parts of a device shown in FIG. 9.
Figure 12:
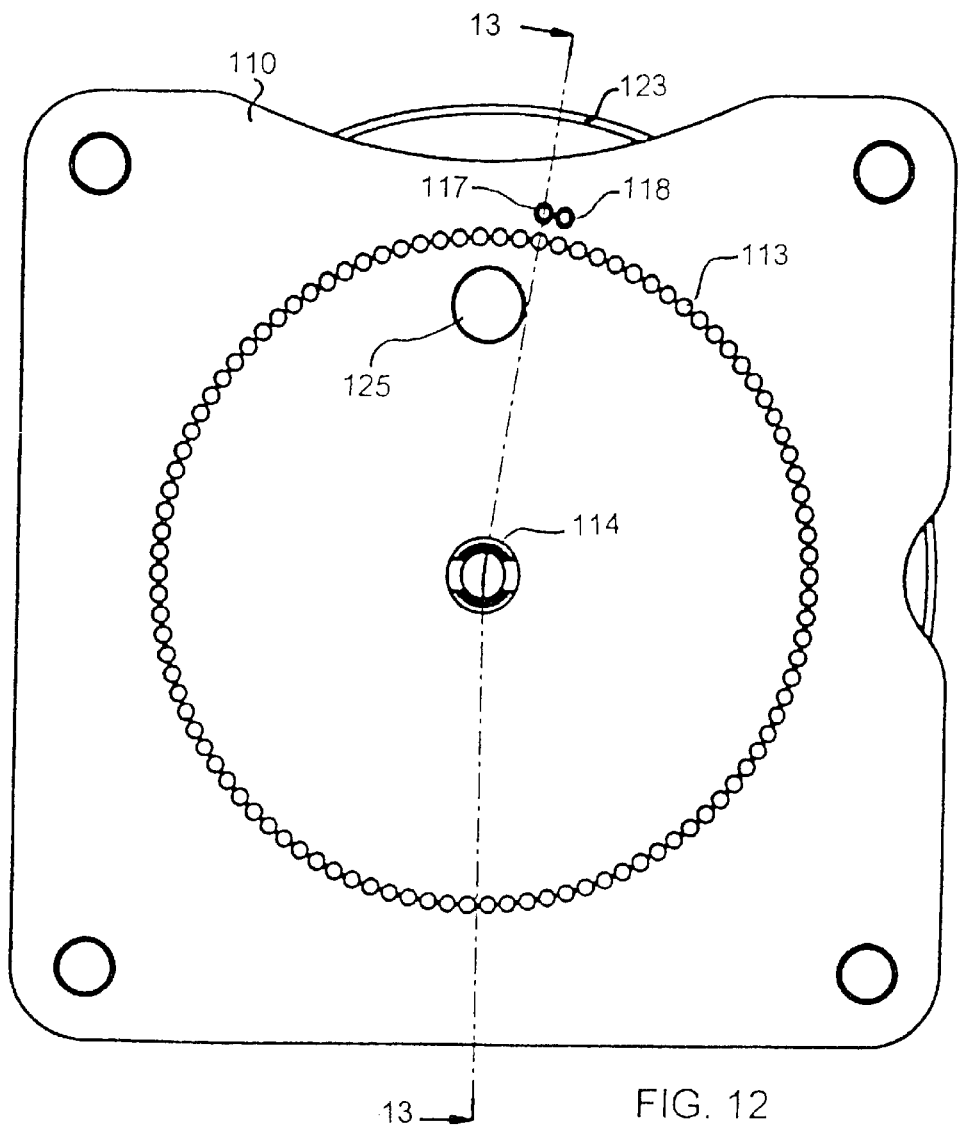
FIG. 12 shows a front view of a seed supply container.

FIG. 9 shows another embodiment of a device according to the invention. For clarity a housing has not been shown. The device 100 comprises a pushing drive module 101, two supply containers 102a for seeds and 102b for spacers respectively and a seed-spacer train assembly module 103. A flexible tube 104 is connected between the seed-spacer train assembly module 103 and an implant needle 105. A connector 106 such as a Luer connector connects tube 104 to needle 105. A plate 107 supports various elements of the device. A top view of the device is shown in FIG. 10. FIG. 10 further shows a motor 108a for driving the pushing wire, a motor 108b for driving the seed and the spacer storage containers 102a and 102b and a motor 108c for retracting the tube 104 and associated needle 105. Motors 108a, 108b and 108c are controlled by electronic control device 12. Further sub-modules are shown in FIG. 11. The two supply containers 102a and 102b and the pushing module 101 are clamped together to form a single module for assembly to the plate 107. Assembly module 103 comprises a detachable part 103a and a fixed (to plate 107) part 103b.

Figure 14:
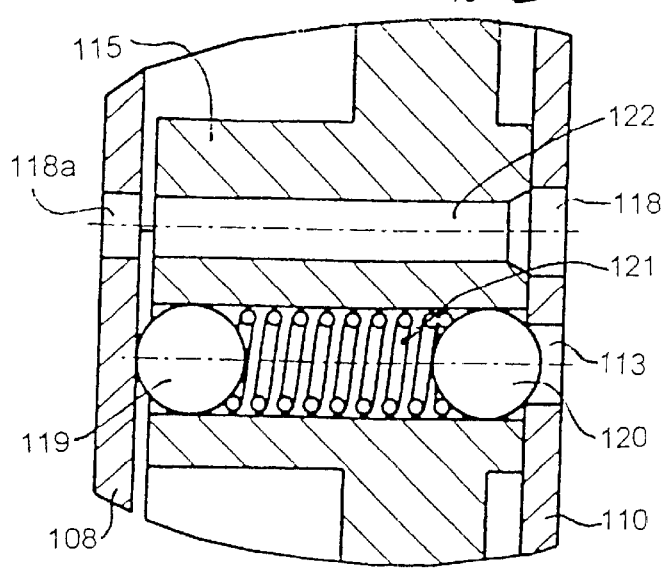
FIG. 14 shows a detail of FIG. 13.
Figure 15:
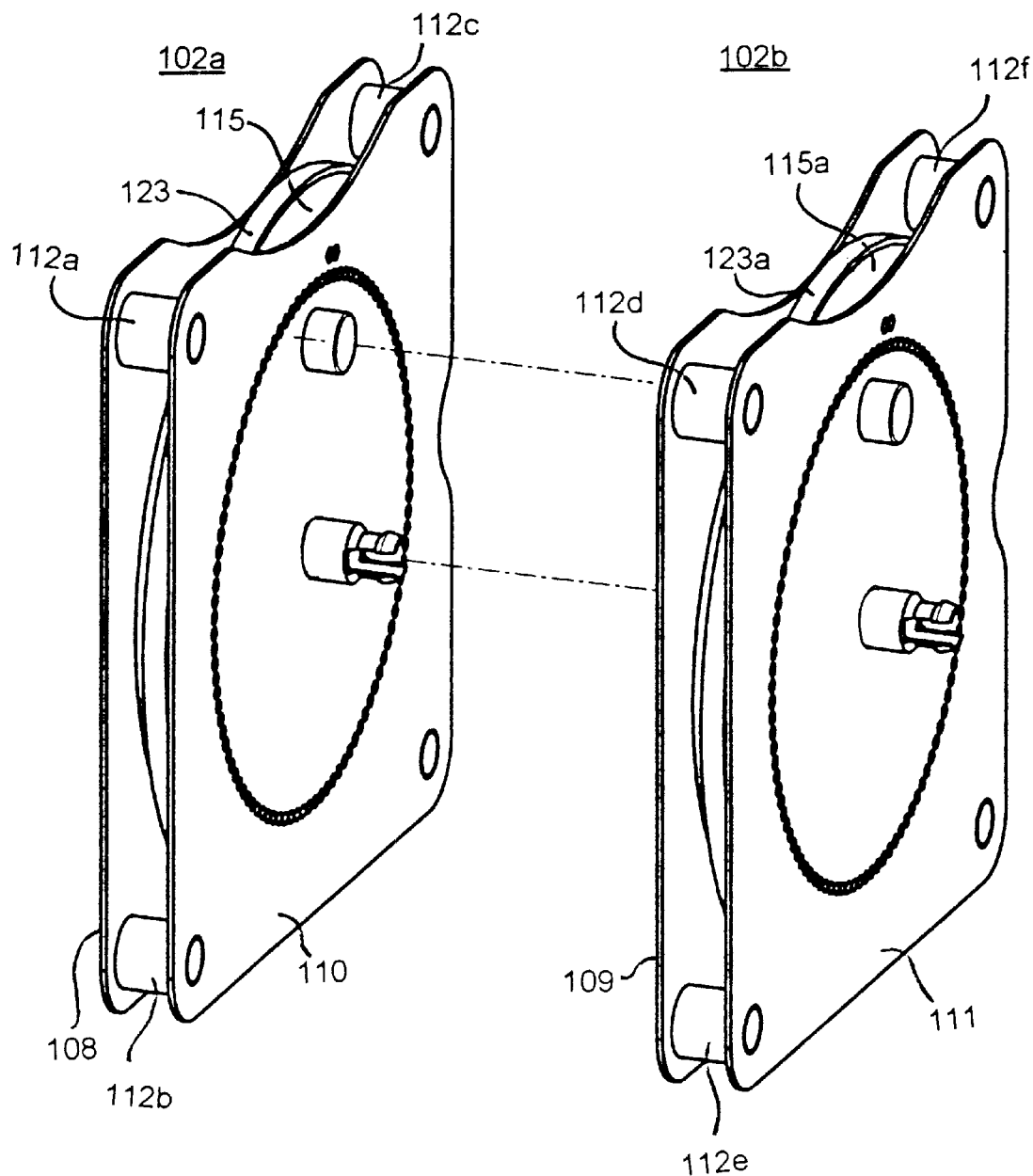
FIG. 15 shows a seed- and a spacer supply container.
Figure 16:
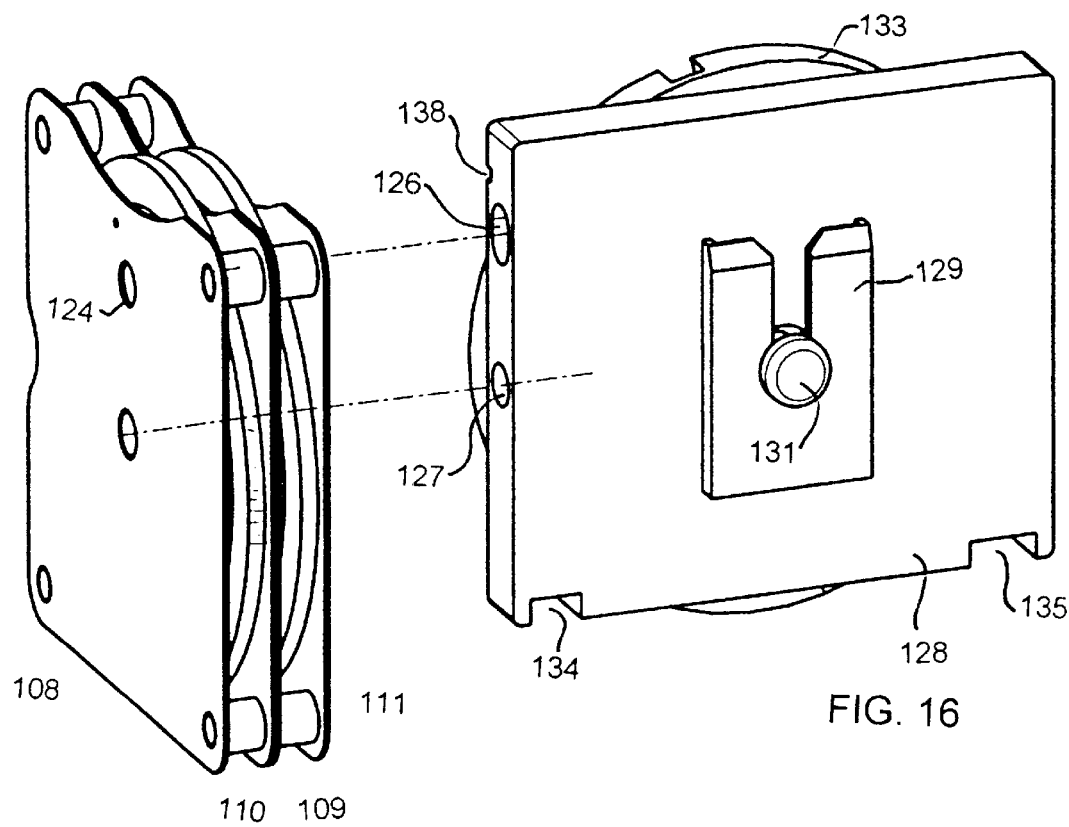
FIG. 16 shows a first view of a connection between the supply containers and the pushing drive module.
Figure 17:
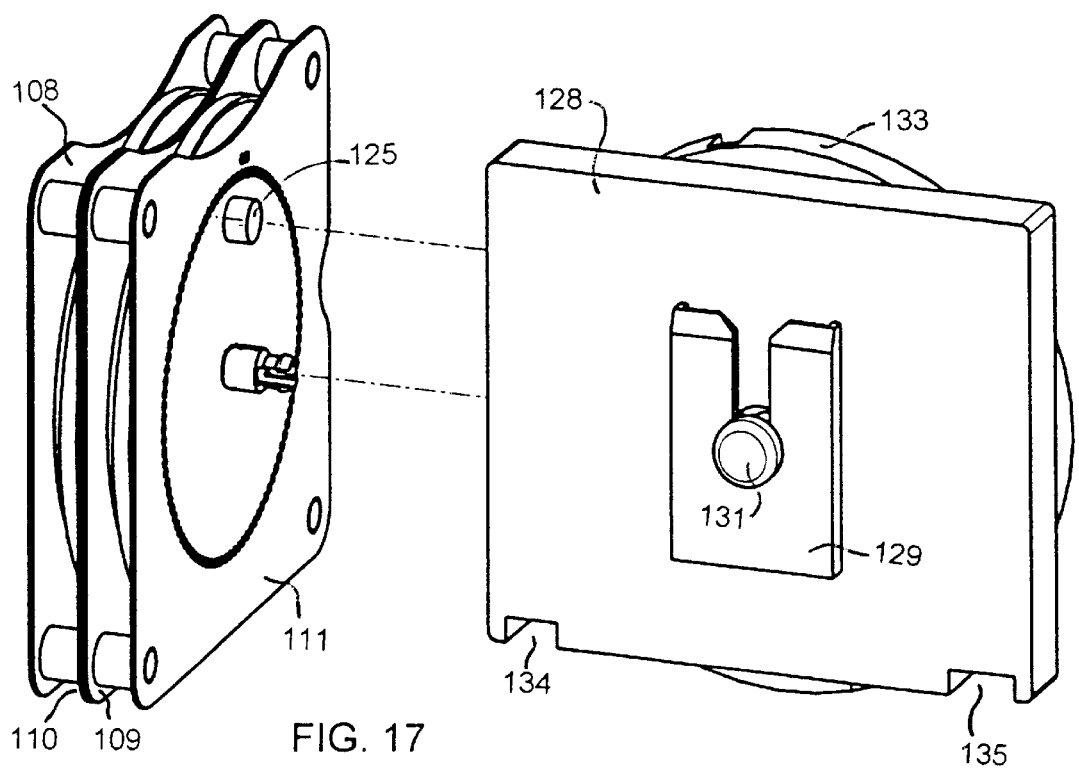
FIG. 17 shows a second view of a connection between the supply containers and the pushing drive module.

FIGS. 12 through 15 show in more detail the construction of the supply containers 102a and 102b. Each of the supply containers 102a and 102b comprises a back plate 108 and 109 respectively and a front plate 110 and 111 respectively. Front and back plates are held together at a specified distance by means of eight bushings six of which are shown as 112a . . . 112f. Circular arrays of openings 113 are provided in each front and back plate. In the center of each circular array of openings 113 a larger opening 114 is present. Between each front and back plate a disk 115 is mounted. Each disk 115 has a center opening through which it fits over a snap-fit coupling 116. Each disk 115 is provided with teeth 123 so that it may be driven to rotate about snap-fit coupling 116. The diameters of the openings 114 and the outer dimensions of the snap-fit couplings 116 are such that the couplings 116 fit snugly but are freely rotatable in the openings 114. Each of the front and back plates is further provided with a set of openings 117 and 118 at a slightly larger radius than the openings 113. As shown in FIG. 14 each disk 115 is provided with a set of two balls 119 and 120 and a spring 121. The sets of balls 119, 120 and springs 121 are at a radius that is equal to the radius of the openings 113. Thereby the disks 115 may be rotationally fixed in position upon ball 120 coinciding with an opening 113. Each of the disks 115 with a series of bores 122 at the same radius as openings 117 and 118. The angular distance between subsequent bores 122 in disks 115 is equal to the angular distances between subsequent openings 113 in the front and the back plates 108, . . . , 111. Each bore 122 may house one seed or spacer. As shown more clearly in FIGS. 16 and 17 each back plate 108 and 109 respectively is provided with an opening 124 and each front plate 110 and 111 respectively is provided with a cam 125. By bringing supply containers 102a and 102b together in the way shown in FIGS. 16 and 17 cam 125 of supply container 102a on front plate 110 fits into opening 124 in back plate 109 of supply container 102b. At the same time snap-fit coupling 116 of supply container 102a snap-fits into snap-fit coupling 116 of supply container 102b. Thereby both supply containers 102a and 102b form a single supply container module. Cam 125 and snap-fit coupling 116 of front plate 111 furthermore fit into openings 126 and 127 respectively of support plate 128 of pushing drive 101. As shown in FIGS. 16–20 pushing drive 101 comprises a support plate 128, a fixing plate 129, a multi-diameter shaft 130 with a top 131, a pushing wire 132 and a wire storage wheel 133. The support plate 128 is provided with support notches 134 and 135 and a central opening 136. Support plate 128 further is provided with a straight groove 138. The height and width of groove 138 are essentially the same as the diameter of pushing wire 132. Multi-diameter shaft 130 comprises a top 131 of a diameter at most as large as the diameter of opening 136 in support plate 128. Top 131 is followed by a first part of a first diameter that is smaller than the diameter of the top 131, by a second part of a diameter that is substantially equal to the diameter of the opening 136, by a third part of a diameter that is larger than the diameter of the opening 136 and a fourth part with a still larger diameter. Wire storage wheel 133 comprises a groove 137. The width of the groove 137 is equal to the diameter of the pushing wire 132. The depth of the groove 137 is equal to several diameters of the pushing wire 132. The radius of the groove 137 is equal to the distance from the center of the opening 136 to the groove 138. One end of the pushing wire is fixed in the groove 137. The pushing wire 132 is contained in the groove 137 except for its other end. The other end of wire 132 runs from groove 137 into groove 138. Wheel 133 is provided with two, in this exemplary embodiment diametrically opposed, notches, one of which is visible as 139. As shown in FIG. 11 a driveable wheel 140 is provided with two cams 141 and 142. When wheel 133 is placed against wheel 140 the cams 141 and 142 fit in the notches 139 in the wheel 133. As shown in FIG. 10 wheel 140 is driveable by motor 108a. Pushing drive module 101 is assembled from the various parts as shown in FIG. 18. After the pushing drive module has been assembled and the supply containers 102a and 102b have been assembled all three are assembled together to provide a module as shown in FIG. 11. After assembly of the module of the pushing drive module 101 and the supply containers 102a and 102b that module is mounted such that the notches 134 and 135 fit in corresponding notches in pins 143 and 144 (FIG. 11). A screw in pin 145 fixes support plate 128 in position. In positioning the module care should be taken that the cams 141 and 142 fit in the notches 139. Upon placement of the module also the teeth 123 and 123a of wheels 115 and 115a respectively mesh with teeth on a shaft (not shown) of motor 108b. Groove 138 now is aligned with openings 118 and 117 and corresponding openings in supply container 102b.

Figure 21:
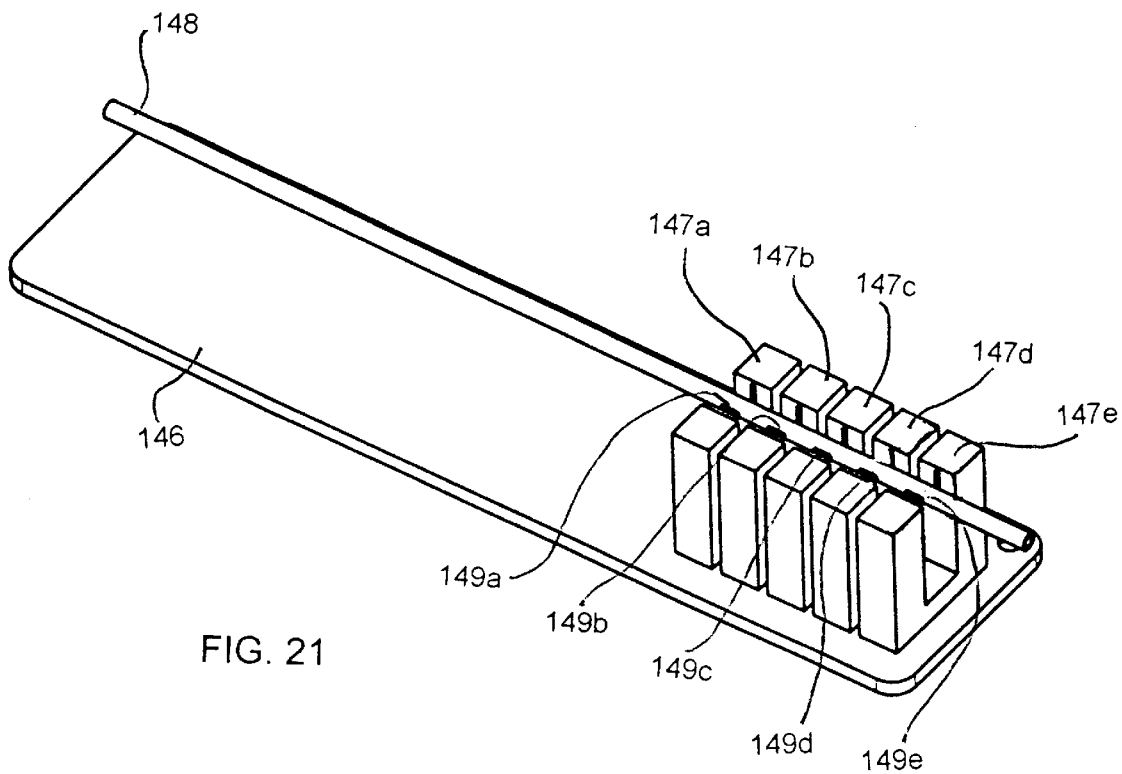
FIG. 21 shows part of the assembly module.
Figure 21A:
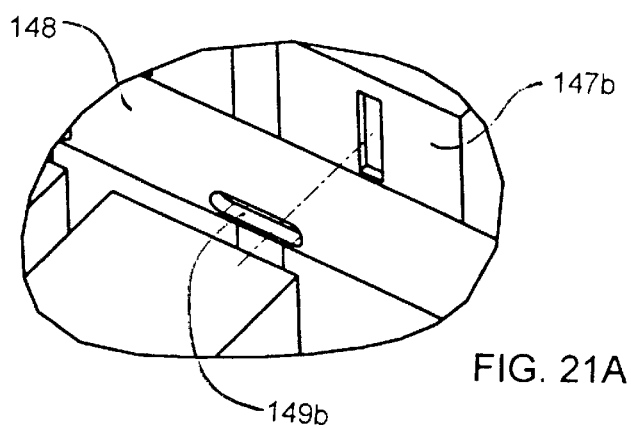
FIG. 21A shows a detail of FIG. 21.
Figure 22:
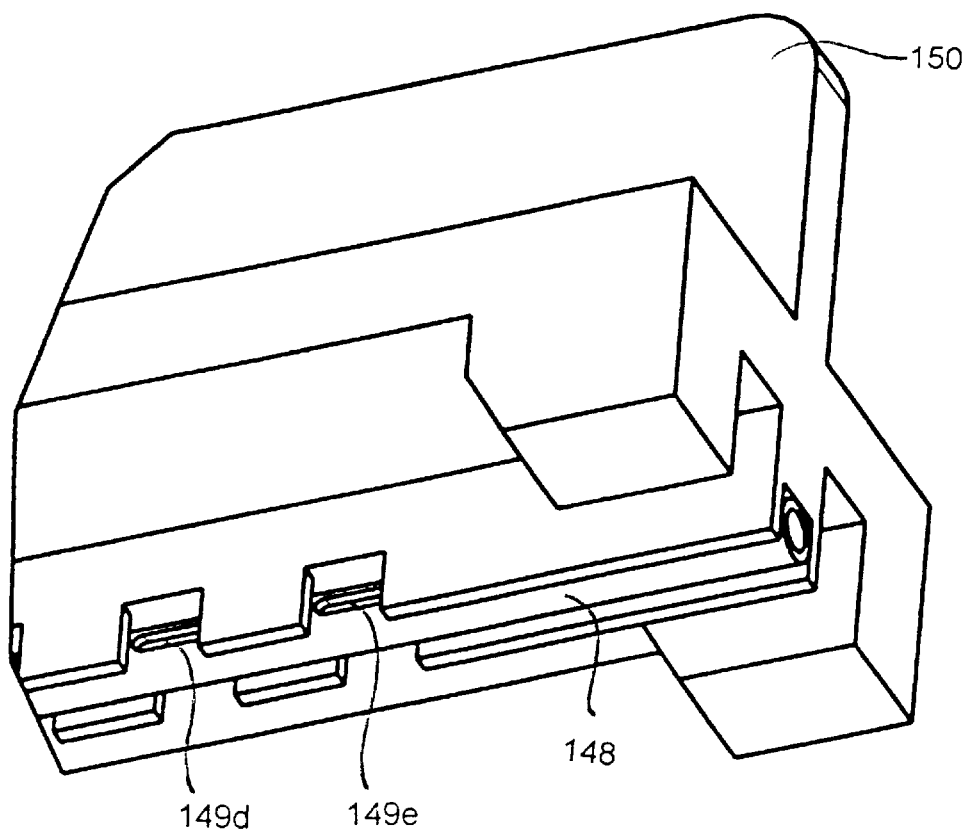
FIG. 22 shows a detail of a part of an assembly module.
Figure 24:
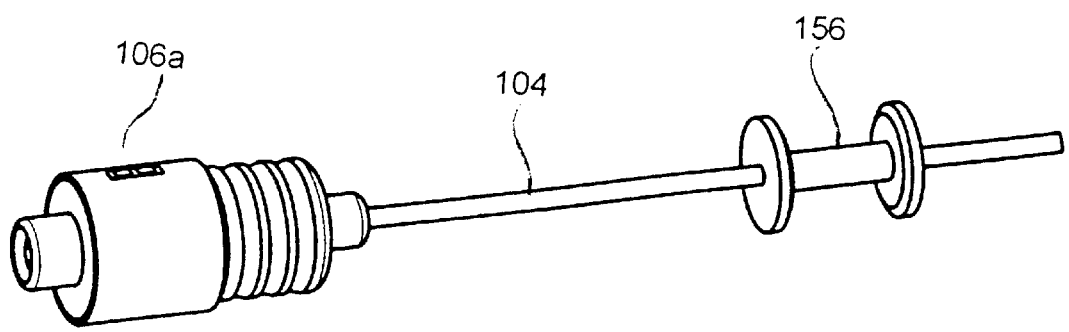
FIG. 24 shows a tube with connector.

A relevant detail of assembly module 103 is shown in FIG. 21. A platform 146 is fixedly positioned in a groove 151 of part 103b (FIG. 11). On platform 146 a number of opto-couplers 147a, . . . , 147e are mounted, in the exemplary embodiment shown in FIG. 21 the number is five. The number, however, may be more or less. Opto-couplers 147 are connected to electronic control device 12. Also shown in FIG. 21 is tube 148. Tube 148 is part of detachable part 103a but has been shown here for clarity. Tube 148 is provided with a number of opposing openings 149a, . . . , 149e. Upon insertion of detachable part 103a in the assembly module 103 the openings 149a, . . . , 149e are in the lines of sight of the opto-couplers 147a, . . . , 147e as shown more clearly in FIG. 21A. Also then the proximal end of tube 148 is in longitudinal alignment with openings 118 and 118a in supply container 102a. FIG. 22 shows in more detail how tube 148 forms part of detachable part 103a. Detachable part 103a is an elongate element with a dorsal fin 150. Detachable part 103a fits into longitudinal groove 151 in part 103b. Upon insertion of part 103a in groove 151 tube 148 is positioned as shown in FIG. 21.

Tube 104 is provided with a dumb-bell like element 156 that is attached to it in a non-sliding way, e.g. by gluing. At its distal end tube 104 is provided with a connector 106a. Dumb-bell like element 156 snaps in a notch 152 in pin 153. Pin 153 is mounted at a distal end of a toothed bar 154. The teeth of toothed bar 154 mesh with a gear-wheel 155 mounted on a shaft of motor 108c. Toothed bar 154 slides in housing 103c. Tube 104 has a length of about 30 centimeter and is made of a nickel-titanium alloy. Thereby tube 104 is very flexible without risk of breaking or kinking. It may be connected with various implant needles 105 without having to displace device 100. At its proximal end tube 104 fits slidingly over the distal end of tube 148. Tube 148 is slid into tube 104 upon insertion of detachable part 103a into groove 151.

Figure 23A:
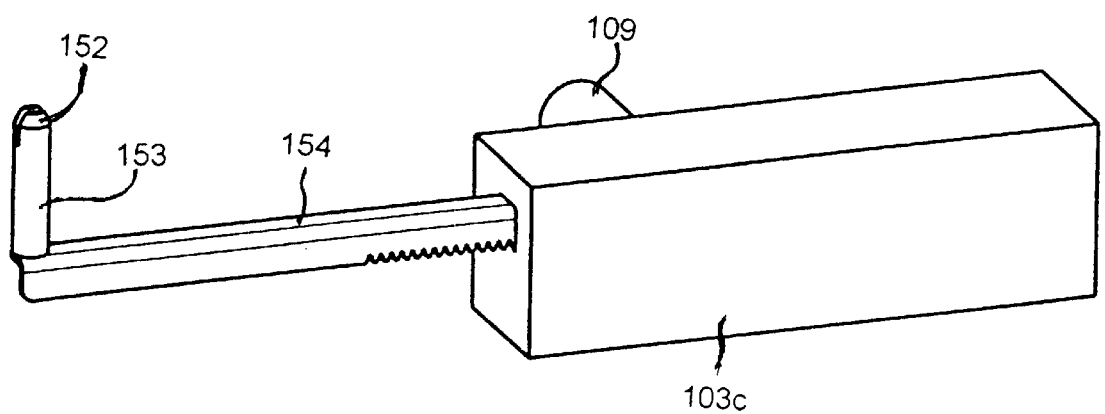
FIGS. 23A and 23B show views of the retracting mechanism in the embodiment according to FIG. 9.
Figure 23B:
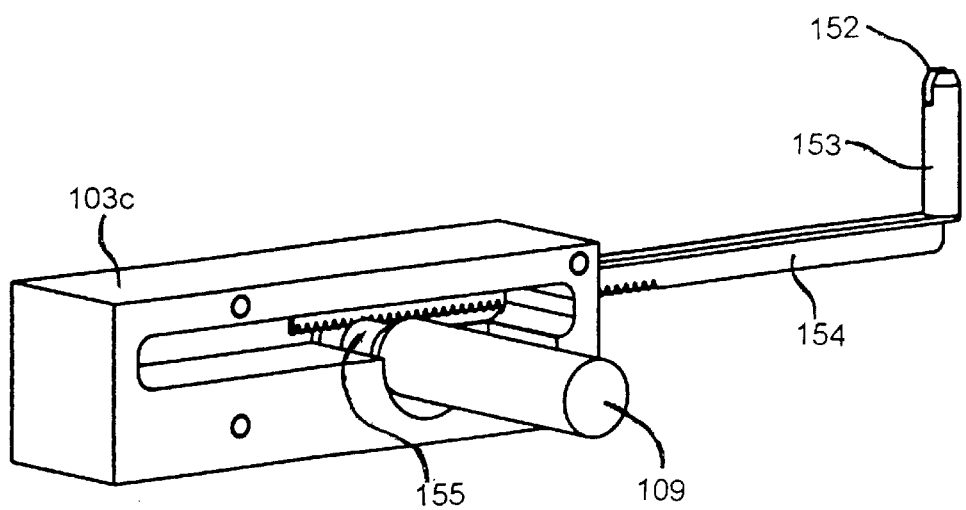

Upon operation of the device 100 first a seed supply container 102a and a spacer supply container 102b are filled with seeds and spacers respectively and coupled together. Subsequently both are coupled to pushing module 101. Next the module thus assembled is mounted into position on pins 143 and 144 and fixed in position by means of the screw in pin 145. Further detachable part 103a is inserted into groove 151 under concurrent fitting tube 104 over tube 148. Toothed bar 154 is in its OUT position, i.e. a position as shown in FIG. 23B. From that position toothed bar 154 may be moved inwardly only to its IN position, in which IN position it may not be moved to the left in FIG. 23B anymore. Under control of electronic control device 12 motor 108a is activated to rotate wheel 140 such that wire 132 is driven out of module 101. Due to the alignment of groove 138 with openings 118 and 118a the wire 132 pushes the spacer and the seed present in the corresponding openings 122 into the tube 148. It may be noted that a spacer seed set may also consist of only a spacer or only a seed depending on the required radiation distribution as determined by the therapy planning module 12a in the pre-plan. Opto-couplers 147 detect the passage of the seed-spacer pair until it reaches the distal opto-coupler 147a. Then the wire 132 is retracted into groove 138. Next the seed and spacer supply containers 102a and 102b are rotated one step by means of motor 108b. Then again motor 108a is activated to move wire 132 to push a second seed-spacer pair into tube 148. Presence of the second seed-spacer pair is detected by opto-coupler 147b. Again the wire 132 is retracted and a third seed-spacer pair may be inserted into tube 148. This continues until all seed-spacer pairs are present in tube 148 thereby making up a seed-spacer train. Tube 104 now is or already was connected to the needle for which the seed-spacer train was intended. After the last seed-spacer pair had been introduced into tube 148 wire 132 had not been retracted anymore. Motor 108a now is controlled to move wire 132 further out. Thereby the seed-spacer train that had been built up in tube 148 is moved through tube 148 into tube 104 and further into needle 105 until it reaches the distal end of needle 105. As described before needle 105 is an open needle with a wax plug at its distal end. Since all elements have predetermined dimensions it is easy to control motors 108a, 108b and 108c such that the seed-spacer train stops just in front of the wax plug. The motors 108a, 108b and 108c may thereto be provided with known coding disks or may be stepper motors. After the seed-spacer train has been delivered into the distal end of the needle 105 just in front of the wax plug wire 132 is kept in that position. Next motor 108c is energized to move toothed bar 154 to the right in FIG. 23A. Thereby pin 153 through dumb-bell like element 156 reracts tube 104 and needle 105. Tube 104 then slides over tube 148. Alternatively since tube 104 is made of such a flexible material a slack may form between pin 153 and tube 148 thereby doing away with the requirement that tube 104 slide over tube 148.

Next tube 104 is coupled to a next needle and the operation described hereinabove is repeated. That continues until all seed-spacer trains have been delivered into the prostate gland 111. Then tube 104 is decoupled from the last used needle. Subsequently all needles are removed from the body for sterilization or disposal.

Figure 28:
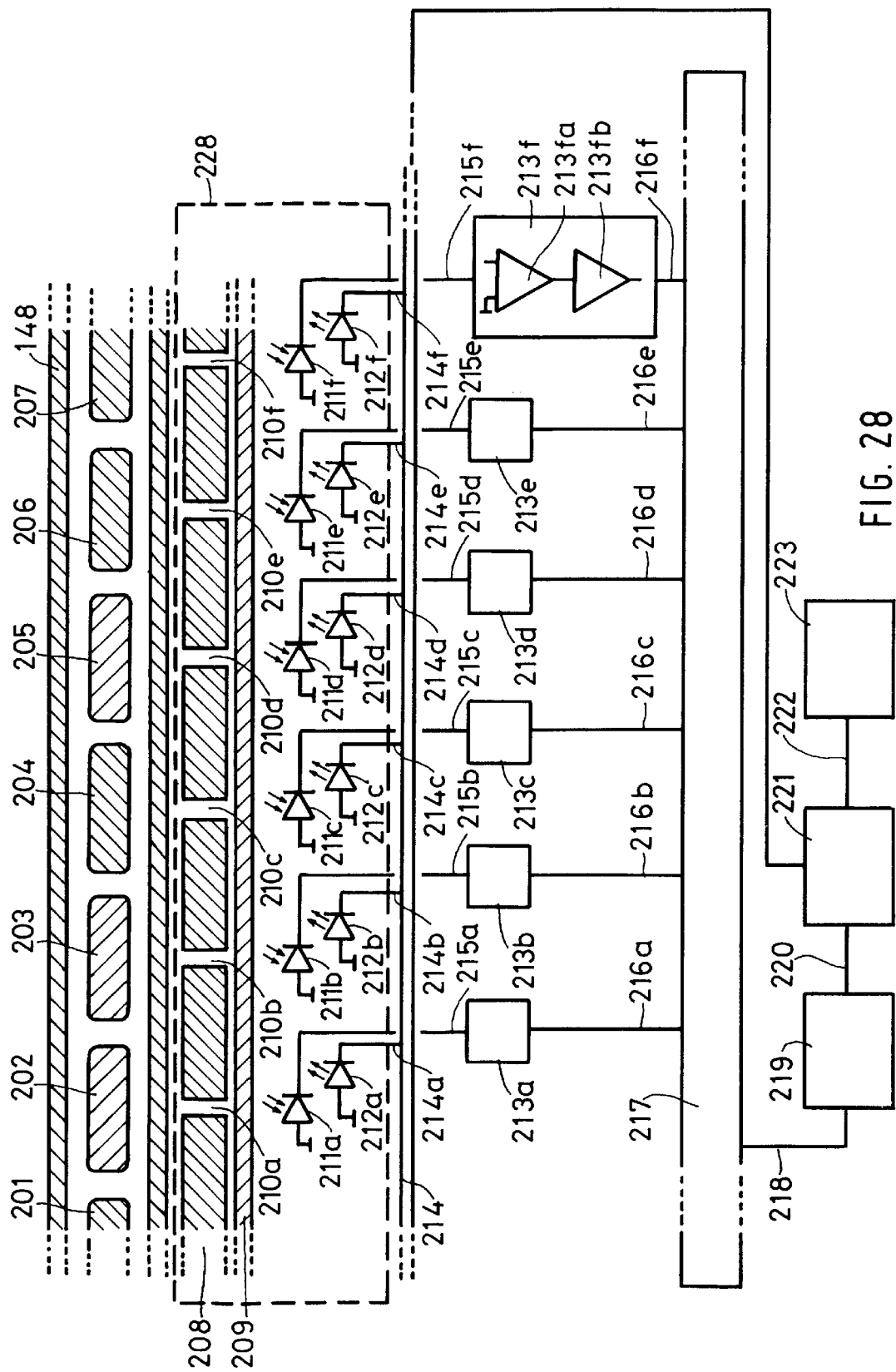
FIG. 28 shows a detail of the assembly module.

FIG. 28 shows a detail of the assembly module. In FIG. 28 tube 148 is shown. In the tube 148 four seeds 201, 204, 206 and 207 are shown as well as three spacers 202, 203 and 205. Along a length of the tube 148 corresponding to a maximum length of a train of seeds and spacers that can be accommodated in a needle a collimator 208 has been arranged. Collimator 208 has been manufactured of a material that is "not" penetratable by the radiation emitted by the seeds 201, 204, 206 and 207. The collimator 208 is provided with openings some of which have been shown as 210a, 210b, 210c, 210d, 210e and 210f. Behind the collimator 208 a sheet 209 of scintillating material has been arranged. The sheet 209 emits light when it is hit by radiation from a seed in the tube 148. Aligned with the opening 210a, . . . , 210f radiation sensitive elements 211a, . . . , 211f have been installed. The radiation sensitive elements 211 have been shown here by way of example as radiation sensitive diodes. Each of the radiation sensitive elements 211a, . . . , 211f is connected via a corresponding line 215a, . . . 215f to a corresponding amplifier 213a, . . . , 213f. As shown in more detail with respect to amplifier 213f each amplifier comprises an input amplifier 213fa and a further amplifier 213fb. Via corresponding lines 216a, . . . , 216f each of the amplifiers 213a, . . . , 213f is connected to a multiplexer 217. An output line 218 of multiplexer 217 is connected to analog-digital converter 219, an output of which is connected via line 220 to a microprocessor 221. Via line 222 microprocessor 221 is connected to a display 223. As indicated by dashed line 228 the collimator 208, the scintillator sheet 209 and the radiation sensitive elements 211a, . . . , 211f are enclosed in a light tight housing. Inside the light tight housing 228 each of the radiation sensitive elements 211a, . . . 211f may not only receive radiation emitted by scintillating material 209 in response to radiation received through an opening 210 from a radioactive seed but may also receive radiation from a corresponding radiation emitting element 212a, . . . 212f. By way of example the radiation emitting elements 212a, . . . , 212f have been shown as light emitting diodes. Each of the radiation emitting elements 212a, . . . , 212f is connected to microprocessor 221 via a bus 214.

By energizing each of the radiation emitting elements 212a, . . . , 212f via bus 214 microprocessor 221 may detect whether corresponding radiation sensitive elements 211a, . . . , 211f respond in a required way to the presence of radiation.

In operation the seeds 201, 204, 206 and 207 and spacers 202, 203 and 205 are pushed into the tube 148 by means of the pushing drive 101 in accordance with the pre-plan for assembling trains of radioactive seeds and non-radioactive spacers for implantation. Distances between openings 210a, . . . , 210f correspond to the distances from a first seed or spacer to a next seed of spacer, such as shown in FIG. 28 in which each seed or spacer 202, . . . , 207 corresponds to an opening 210a, . . . , 210f. When a seed or spacer is placed in a train in the tube 148 in the assembly unit 103 microprocessor 221 is able to determine whether at a certain location a radioactive seed or a non-radioactive spacer is present. In case a seed is present a radiation sensitive element 211 will emit a signal, in case a spacer is present a radiation sensitive element 211 will not emit a signal.

From time to time the radiation sensitive elements 211 are checked for correct operation by energizing the radiation emitting elements 212. After the train of seeds and spacers has been assembled in the tube 148 and it has been determined by the microprocessor 221 that said seeds and spacers are present in the correct order the seed-spacer train is moved through tube 148 into tube 104 and further into needle 105 until it reaches the distal end of needle 105, one and another as has been described hereinbefore.

Figure 29:
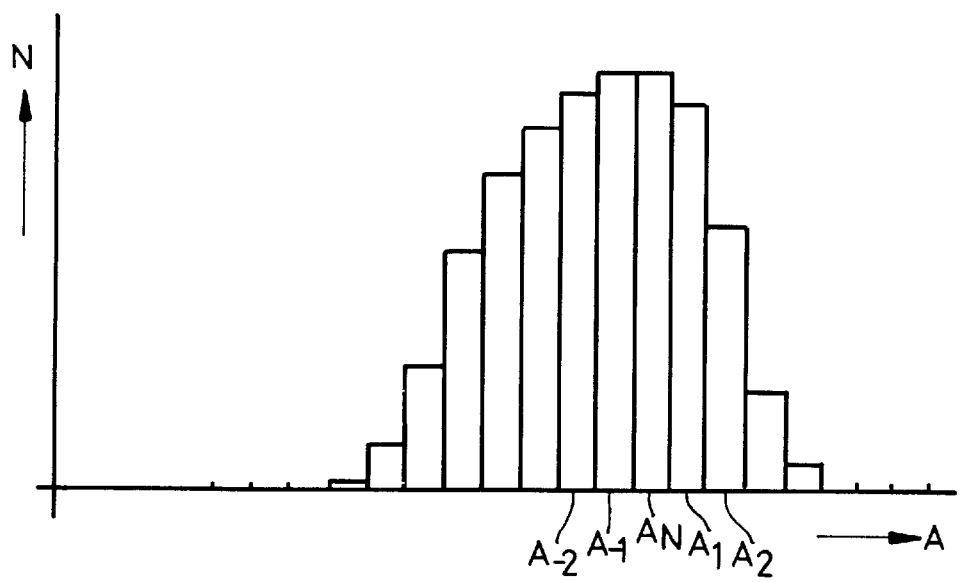
FIG. 29 shows a distribution of activities of seeds at a specified nominal activity.

Radioactive seeds are delivered by a manufacturer as having a specified nominal activity. Nevertheless there is a tolerance range about the specified nominal activity within which activities of seeds may be without being considered not to be of the specified nominal activity. FIG. 29 shows an example of how the number of seeds for certain activities about a specified nominal activity $A_N$ may be distributed. The distribution example shown in FIG. 29 is a little bit skewed with more seeds having an activity lower than the specified nominal activity and less seeds having an activity over the specified nominal activity. As a consequense a supply of seeds having been delivered with the specified nominal activity $A_N$ may, in a specific seed spacer train in the tube 148, be made up of seeds having various levels of activity. It may even be that all of the seeds in a certain seed-spacer train have activities lower than the specified nominal activity or that a certain part of such trains has only seeds with a lower activity whereas another part of said train has only seeds of a higher activity. All kinds of distribution of seeds with various activities, though with the same specified nominal activity, are imaginable. The embodiment shown in FIG. 28 is able to distinguish between the various levels of activity about the nominal activity $A_N$. Such levels have been identified by way of example as $A_{-2}$, $A_{-1}$, $A_1$, $A_2$, ... in FIG. 29. Microprocessor 221 stores for each seed-spacer train that has been assembled in tube 148 and has been implanted in the animal body the activities of the individual seeds 201, 204, 206 and 207 as well as their locations in the seed-spacer trains for use by the therapy planning module 12a (FIG. 1) to recalculate the pre-plan. As is well-known the pre-plan has originally been determined making use of the specified nominal activity. Now that the seed spacer trains have been made up and the actual activities of the individual radioactive seeds have been determined it is possible to determine the differences in the dose distribution according to the pre-plan and the dose distribution that is to be expected from the actual activities of the seeds. Often the determination of the pre-plan is done with taking the activities of all radioactive seeds to be the same and equal to the specified nominal activity. The recalculation described hereinabove may therefor also take place by taking an average value of the seeds that have actually been implanted.

A still better recalculation may be done if not only the actual activities of the implanted seeds are taken into consideration but also the actual locations in which the seeds have been placed. As described hereinbefore said actual locations of the implanted seeds may be determined under CT-imaging fluoroscopy or another method reconstructing the individual seeds.

Recalculation of a pre-plan based upon actual locations of implanted seeds and activities of those implanted seeds is known as such from U.S. Pat. No. 6,129,670 to Burdette et al. Therein has been described the use of radioactive seeds of two different specified nominal activities. Differential measurements relating to various activities about those specified nominal activities and analyzing amount of activity taking into consideration a tolerance region about each specified nominal activity are not disclosed in that patent.

Figure 30:
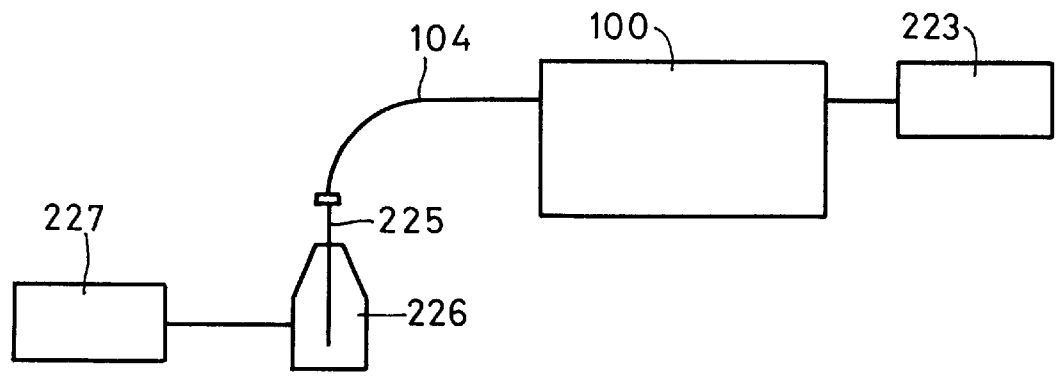
FIG. 30 shows a calibration measurement.

FIG. 30 shows a way to calibrate the device shown in FIG. 28. Thereto the tube 104 is connected to a needle 225 of a calibrating device 226. A control device 227 controls the calibrating device 226. Calibrating device 226 with corresponding needle 225 and control 227 may for example be a well-type ionisation chamber, manufactured and marketed by Standard Imaging of Middleton, Wis., USA, under the indication Eclipse.

A calibration of the device shown in FIG. 28 takes place as follows. One seed is used to calibrate the radiation detector array shown in FIG. 28 by positioning that seed in front of each collimator opening 208a, ..., 210f. Thereby output signal of the radiation sensitive elements 221a, ..., 221f and/or of the amplifiers 213a, ..., 213f are determined by the microprocessor 221. Subsequently that seed is driven in a needle 225 which is placed inside the well-type chamber of the calibrating device 226. Preferably the calibrating device 226 has a calibration against a so-called secondary standard. The result of the activity measured by the calibrating device 226 is read from display 227. The result shown on display 227 than is input, either by hand or automatically, in the microprocessor 221 (not shown). Thereby the readings of the radiation sensitive elements 211a, ..., 211f are normalized to the activity level measured in the calibrating device 226. After the calibration microprocessor 221 shows activities of seeds 201, 204, 206 and 207 in units as in the so-called cross calibration in the calibrating device 226.

Figure 31:
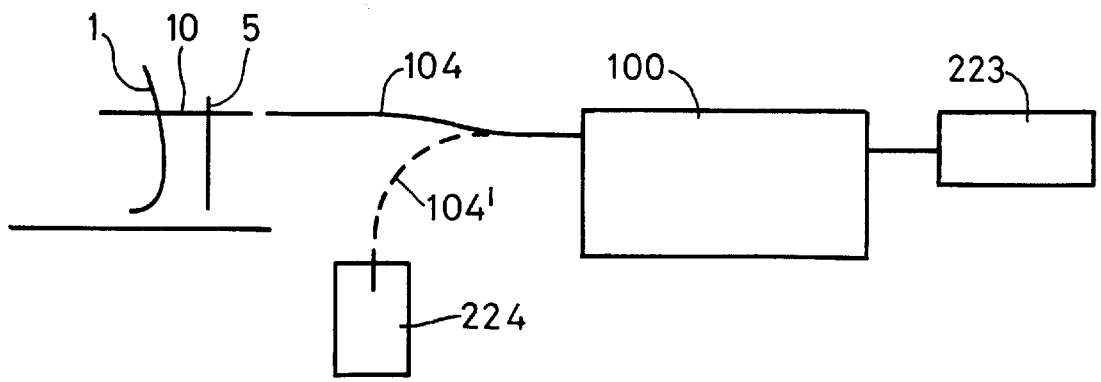
FIG. 31 shows schematically disposing of incorrect trains.

The device shown in FIG. 28 opens up the further possibility of handling trains of seeds and spacers. Said further possibility is shown schematically in FIG. 31. FIG. 31 shows in drawn line the tube 104 connected to a needle 10. When assembling a seed-spacer train in the tube 148 the microprocessor 221 is able to determine whether the train under assembly has seeds and spacers in the correct order and/or of the correct activities. If for some reason a seed or a spacer turns up at a location where a spacer and a seed, respectively should have turned up than the composition of that seed-spacer train is incorrect. Such train may not be implanted in the animal body. During composition of said seed-spacer train the device according to FIG. 28 is able to determine whether any additional seed or spacer is actually a seed or a spacer. If a to be added element is a seed in stead of a spacer or vice versa a warning shows up at display 223 indicating to the operator that the tube 104 should be disconnected from the needle 10 and be connected to a container 224 for radioactive seeds, such as indicated by dashed line 104'. After the tube 104 has been connected to the container 224 the operator operates the device 100 such that the pushing wire pushes the incorrect seed-spacer train into and through the tube 104' into the container 224. Thereby an incorrectly composed seed-spacer train is disposed of. An incorrect composition of a seed-spacer train may also come about in case of the use of seeds having more than one specified nominal activity. Such correct composition may then also comprise the intended addition of a seed having an activity that is not in accordance with the pre-plan.

In certain cases additional radiation is needed for the treatment of the animal body. The amount of irradation and the locations where such additional irradiation should take place is amongst other dependent upon the radiation that is to be expected from the implanted seeds.

The same or another therapy planning module as the therapy planning module 12a (FIG. 1) is used to determine a so-called post-plan for evaluation of the treatment result and to base further treatment decisions thereon. In a first embodiment the determination of a post-plan comprises first determining a pre-plan for radiation treatment of the animal tissue based upon specified nominal activities of to be implanted radioactive seeds, thereafter assembling trains of said seeds and spacers for implantation in accordance with the pre-plan, determination of the radiation activity of each seed whilst such seed is added to a train of seeds and spacers and determining the post-plan making use of the actually determined radiation activities instead of the specified nominal activity.

A second embodiment of determining a post-plan comprises determining a pre-plan as hereinbefore and assembling trains of seeds and spacers and determining radiation activity of each seed whilst such seed is added to a train as described hereinbefore, further implanting unloaded needles in the animal tissue to be treated, the assembling of the train taking place outside the implanted, unloaded needles in an assembly unit, connecting the assembly unit to an implanted unloaded needle, which may be done before, during or after assembling a train for said needle, transferring an assembled train from the assembly unit to the implanted unloaded needle and implanting the transferred assembled train in the tissue. Than the pre-plan may be recalculated by using determined activities instead of using specified nominal activities and thereafter the host-plan may be determined based upon the recalculated pre-plan. Preferably in recalculating the pre-plan an average value of the determined activities is determined and used.

In the device 100 blood contamination may have taken place of tube 104, tube 148, supply containers 102a and 102b and pushing drive module 101. All those elements are taken out of device 100 for sterilization or disposal.

Depending on what in a certain situation is desired by a hospital those elements may be made of sterilizable material such as stainless steel or of disposable material such as plastics. Present day plastics have such good form stability that it is possible to manufacture the disposable elements with a sufficient degree of accuracy for the present application.

Like with the embodiment shown in FIG. 2 it is possible with the embodiment of FIG. 9 to split up the device 100 in two modules, one a seed loading module for filling a multichannel holder 31 with seed-spacer trains in its channels 33 and a second one a seed implanting module for implanting the seed-spacer trains present in a multichannel holder in an animal body.

Figure 25:
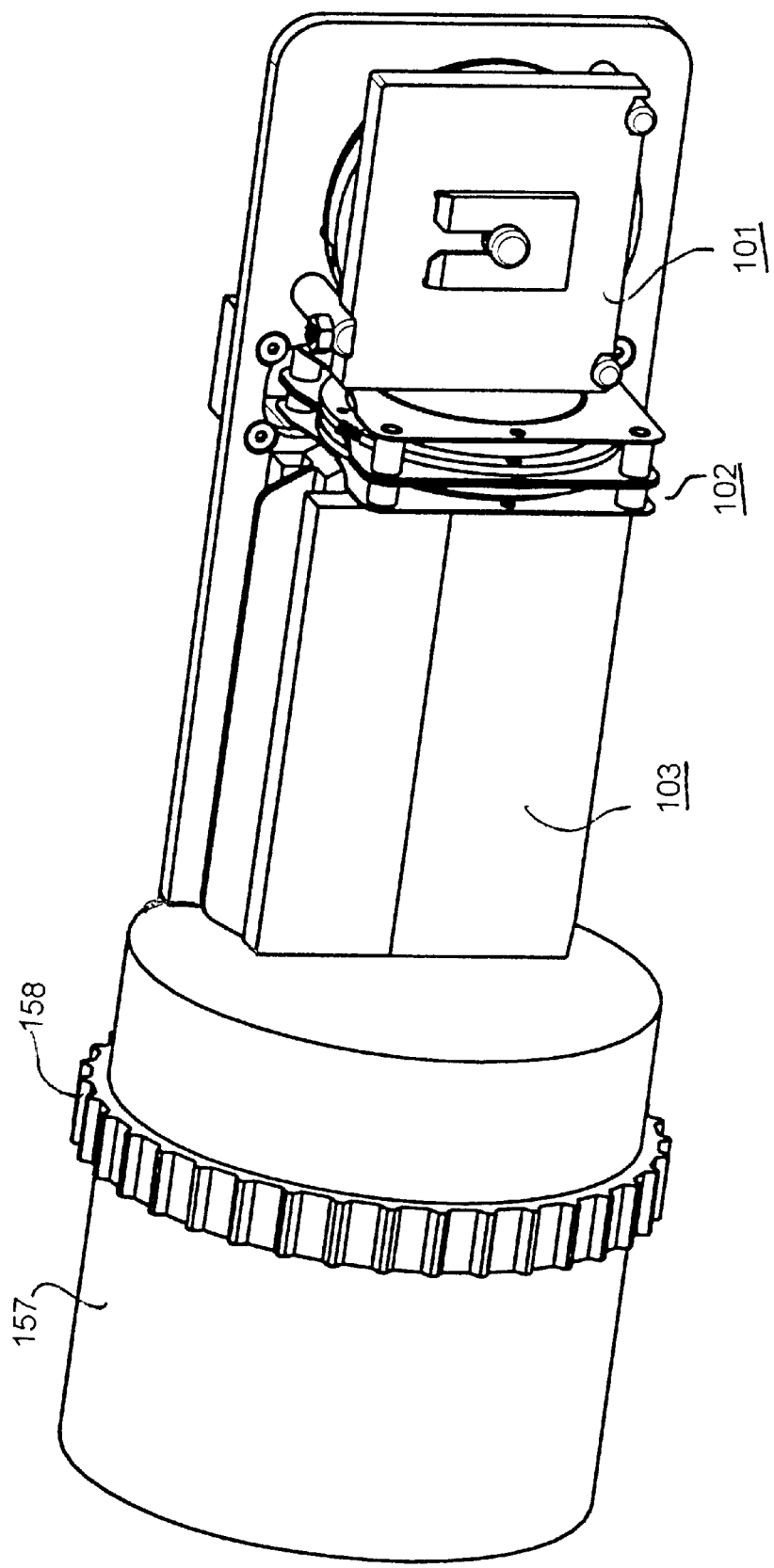
FIG. 25 shows a third embodiment of a seed loading module.
Figure 26:
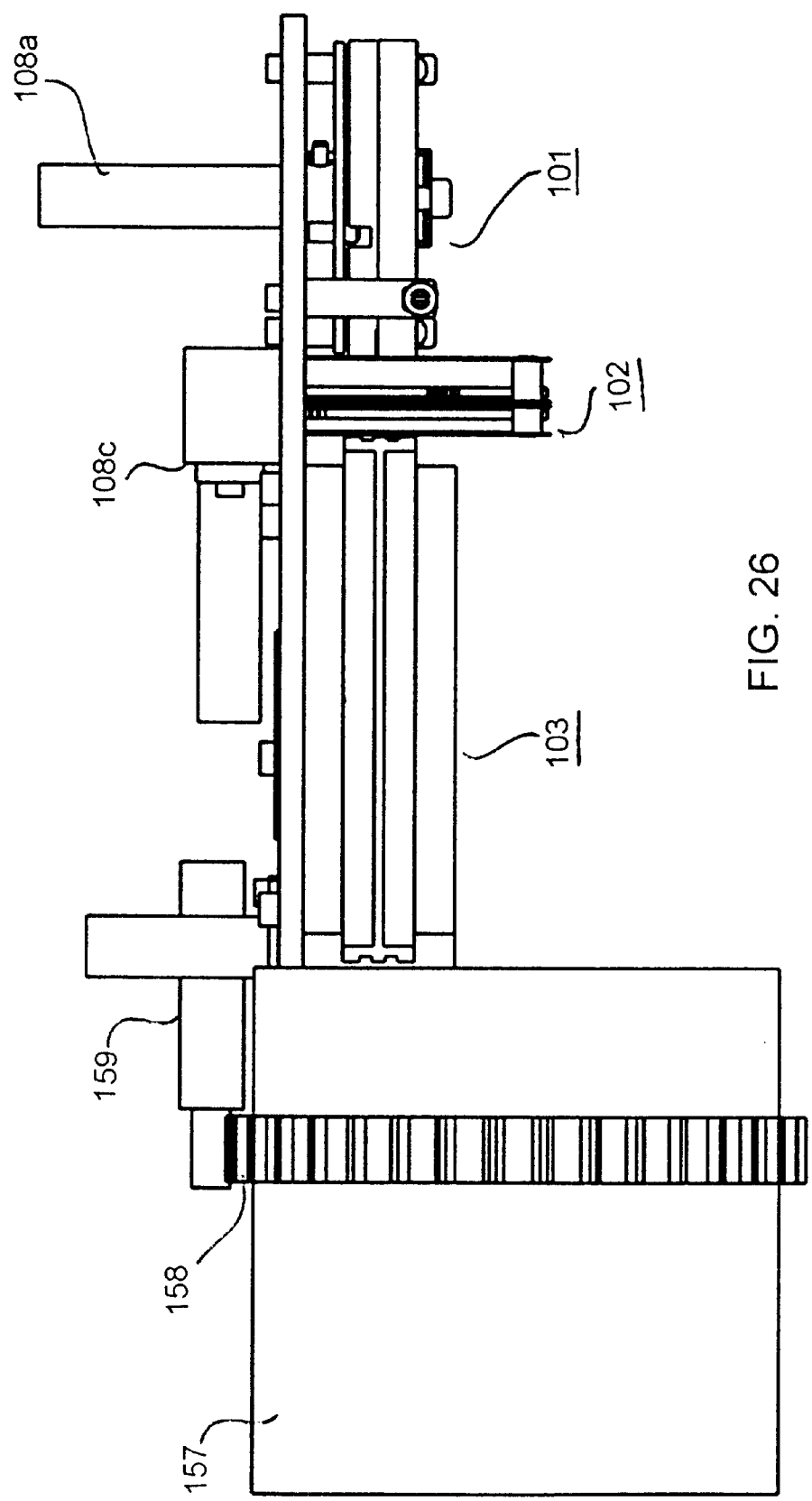
FIG. 26 shows a top view of the part shown in FIG. 25.

FIG. 25 shows such a device with a multichannel holder 157. Multichannel holder 157 is in principle identical to multichannel holder 31 as described hereinbefore in relation to FIG. 2 and now is placed at and connected to the exit of tube 148. Means are provided for rotating multichannel holder 157. Multichannel holder 157 may therefore be provided with a ring of teeth 158 which may mesh upon placement in the device with the teeth of a gear-wheel on a shaft of a motor 159 (FIG. 26).

In order to fill the channels in the multichannel holder 157 the operation of device 100 as hereinbefore described is applicable until the point where the seed-spacer train that has been assembled in tube 148 is pushed into the tube 104. Instead of pushing the seed-spacer train in tube 104 the seed-spacer train is pushed in the channel of multichannel holder 157 that is longitudinally aligned with tube 148. Thereafter motor 159 is energized to rotate multichannel holder 157 such the next available channel is longitudinally aligned with tube 148. Thereafter the next seed-spacer train is assembled in tube 148 and subsequently pushed into the channel in multichannel holder 157. This operation continues until all appropriate channels in multichannel holder 157 have been filled with the appropriate seed-spacer trains.

Figure 27:
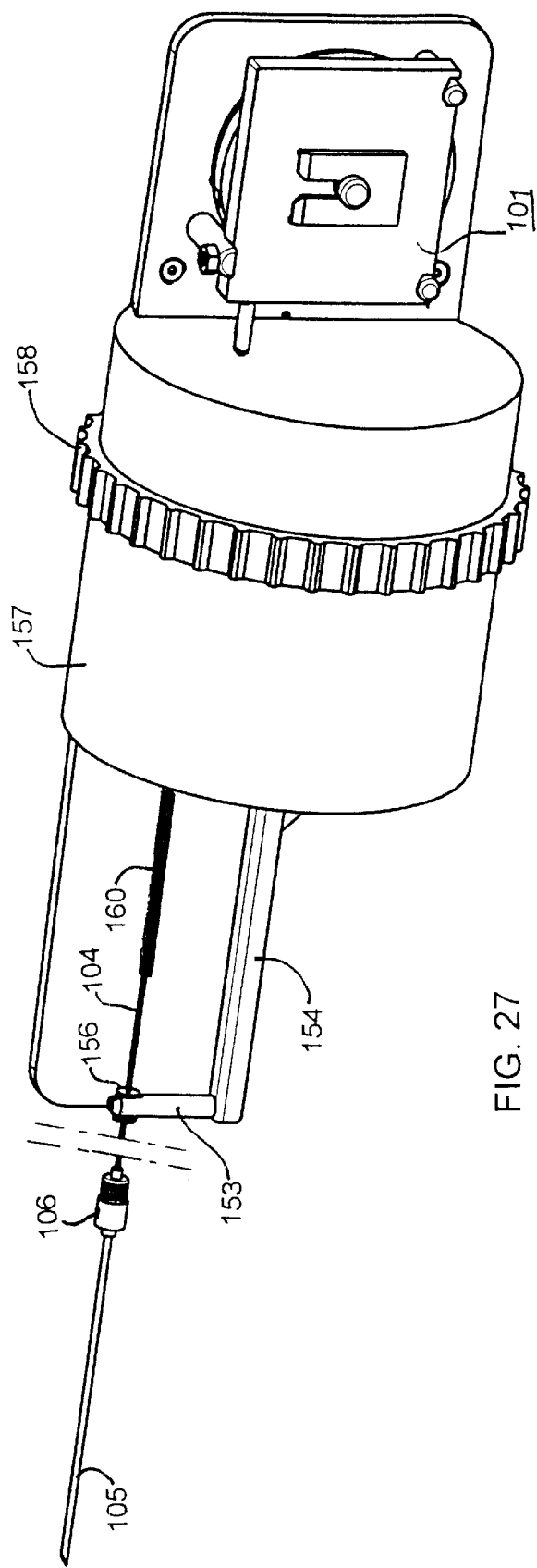
FIG. 27 shows a second embodiment of a seed implanting module.

FIG. 27 shows the device when using the filled multichannel holder 157 for depositing the seed-spacer trains in the body. Instead of the supply containers 102a and 102b multichannel holder 157 is fixed to pushing drive module 101 in essentially the same way as the supply containers 102a and 102b were fixed to that module. Teeth 158 mesh with the teeth of a gear-wheel on a shaft of motor 108a. Between the output side of multichannel holder 157 a fixedly positioned tube 160 is present. Tube 160 fits in tube 104 such that tube 104 is slideable over tube 160. Tube 160 is longitudinally aligned with groove 138 and with the channel in multichannel holder 157 between groove 138 and tube 160.

Operation of the device shown in FIG. 27 for depositing the seed-spacer trains in the body is as follows. Tube 104 is connected to a first needle 105. Multichannel holder 157 and pushing drive 101 are installed. Multichannel holder 157 is rotated such that the appropriate channel with the seed-spacer train for the first needle is longitudinally aligned with tube 160 and groove 138. Then motor 108a and subsequently motor 108c are energized to push the seed-spacer train into the first needle and retract the first needle. After all seed-spacer trains have been delivered in the body all needles are removed from the body, tubes 104 and 160, multichannel holder 157 and pushing drive 101 are removed for sterilization or disposal.

Various embodiments of the invention have been described hereinbefore in which the retracting means for the implant needles were operated by motors under electronic control. Without departing from the scope of the invention it is also possible to operate the retracting means manually, i.e. by moving the elements 60 and 61 respectively by hand.

It should be noted that according to the abovementioned, various modifications may be obvious to a person skilled in the art. Such modifications are deemed to be within the scope of the invention.

What is claimed is:

1. Method for analyzing amount of activity due to radioactive seeds having specified activities and that are to be implanted in animal tissue comprising the steps of:

determining a pre-plan comprising determining a desired distribution of implanted of said radioactive seeds and non-radioactive spacers in said tissue;

in accordance with said pre-plan assembling trains of said radioactive seeds and said spacers for implantation;

accurately determining radiation activity of each seed while adding such seed to a said train with an accuracy that allows distinguishing between different activities within tolerance ranges of said specified activities for such seed.

2. Method according to claim 1, said method further comprising the step of:

recalculating said pre-plan using accurately determined activities.

3. Method according to claim 2, in which the step of using accurately determined activities comprises determining and using an average value of said accurately determined activities.

4. Method according to claim 1, said method further comprising the steps of:

determining actual locations of said seeds after implant; and recalculating said pre-plan using both actual locations and accurately determined activities.

5. Method according to claim 4, in which the step of using accurately determined activities comprises determining and using an average value of said accurately determined activities.

6. Method for implanting radioactive seeds in animal tissue comprising the steps of:

analyzing amount of activity according to claim 1;

implanting unloaded needles in said tissue;

assembling said trains outside said implanted unloaded needles in an assembly unit;

connecting said assembly unit to a said implanted unloaded needle before, during or after assembling a said train for such needle;

transferring said assembled train from said assembly unit to said implanted unloaded needle; and implanting said transferred assembled train in said animal tissue.

7. Method according to claim 6, said method further comprising the step of:

recalculating said pre-plan using accurately determined activities.

8. Method according to claim 7, in which the step of using accurately determined activities comprises determining and using an average value of said accurately determined activities.

9. Method according to claim 6, said method further comprising the steps of:

determining actual locations of said seeds after implant; and recalculating said pre-plan using both actual locations and accurately determined activities.

10. Method according to claim 9, in which the step of using accurately determined activities comprises determining and using an average value of said accurately determined activities.

11. Method according to claim 6, said method further comprising the step of:

during or after assembly and before transfer of a said train checking for correct composition of said train.

12. Method according to claim 11, said method further comprising the steps of;

providing a container for radioactive materials; and in case of a non-correct composition of a said train connecting said assembly unit to said container; and disposing of said not correctly composed train in said container.

13. Method according to claim 1, said method further comprising the steps of:

providing a calibrating device for radiation activity levels;

providing a measuring device for carrying out the step of determining activity of each seed while adding such seed to a train;

calibrating said measuring device against said calibrating device before carrying out the step of determining activity of each seed while adding such seed to a train.

14. Method according to claim 13, said step of providing a calibrating device comprising a step of providing a calibrating device for absolute radiation activity levels.

15. Method for implanting radioactive seeds having specified activities in animal tissue comprising the steps of:

determining a pre-plan comprising determining a desired distribution of implanted radioactive seeds and non-radioactive spacers in said tissue;

in accordance with said pre-plan assembling trains of seeds and spacers for implantation;

determining radiation activity of each seed while adding such seed to a said train;

implanting unloaded needles in said tissue;

assembling said trains outside said implanted unloaded needles in an assembly unit;

connecting said assembly unit to a said implanted unloaded needle before, during or after assembling a said train for such needle;

transferring said assembled train from said assembly unit to said implanted unloaded needle;

implanting said transferred assembled train in said animal tissue.

16. Method according to claim 15, said method further comprising the step of:

recalculating said pre-plan using determined activities.

17. Method according to claim 16, in which the step of using determined activities comprises determining and using an average value of said determined activities.

18. Method according to claim 15, said method further comprising the steps of:

determining actual locations of said seeds after implant; and recalculating said pre-plan using both actual locations and determined activities.

19. Method according to claim 18, in which the step of using determined activities comprises determining and using an average value of said determined activities.

20. Method according to claim 15, said method further comprising the step of:

during or after assembly and before transfer of a said train checking for correct composition of said train being assembled.

21. Method according to claim 20, said method further comprising the steps of;

providing a container for radioactive materials; and in case of a non-correct composition of a said train connecting said assembly unit to said container; and disposing of said not correctly composed train in said container.

22. Method according claim 15, said method further comprising the steps of:

providing a calibrating device for radiation activity levels;

providing a measuring device for carrying out the step of determining activity of each seed while adding such seed to a train;

calibrating said measuring device against said calibrating device before carrying out the step of determining activity of each seed while adding such seed to a train.

23. Method according to claim 22, said step of providing a calibrating device comprising a step of providing a calibrating device for absolute radiation activity levels.

24. Method for determining a post-plan for radiation treatment of animal tissue with radioactive seeds having specified activities, said method comprising:

implanting said seeds according to claim 15;

recalculating said pre-plan using determined activities;

determining said post-plan based upon said recalculated pre-plan.

25. Method according to claim 24, in which the step of using determined activities in recalculating said pre-plan comprises determining and using an average value of said determined activities.

26. Method for determining a post-plan for radiation treatment of animal tissue, said method comprising:

determining a pre-plan for radiation treatment of said animal tissue based upon specified activities of to be implanted radioactive seeds;

in accordance with said pre-plan assembling trains of said seeds and spacers for implantation;

determining radiation activity of each seed while adding such seed to a said train;

determining said post-plan using determined radiation activities.

27. Method according to claim 26, in which the step of using determined activities comprises using an average value of said determined activities.

* * * * *